United States Patent
Watanabe et al.

(10) Patent No.: US 8,067,099 B2
(45) Date of Patent: Nov. 29, 2011

(54) PHOSPHORESCENT MATERIAL, AND ORGANIC ELECTROLUMINESCENT DEVICE AND IMAGE DISPLAY APPARATUS USING SAME

(75) Inventors: Taiki Watanabe, Akishima (JP); Akira Tsuboyama, Machida (JP); Kazunori Ueno, Ebina (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 827 days.

(21) Appl. No.: 12/123,156

(22) Filed: May 19, 2008

(65) Prior Publication Data

US 2008/0299414 A1    Dec. 4, 2008

(30) Foreign Application Priority Data

May 30, 2007    (JP) .................. 2007-142915

(51) Int. Cl.
*H01L 51/54* (2006.01)

(52) U.S. Cl. ........ 428/690; 428/917; 313/504; 313/505; 313/506; 564/426; 564/434

(58) Field of Classification Search .................. 428/690, 428/917; 313/504, 505, 506; 564/426, 434
See application file for complete search history.

(56) References Cited

U.S. PATENT DOCUMENTS

| | | | | |
|---|---|---|---|---|
| 6,097,147 A | 8/2000 | Baldo et al. | | 315/506 |
| 6,303,231 B1 | 10/2001 | Sawada et al. | | 428/470 |
| 6,565,994 B2 | 5/2003 | Igarashi | | 428/690 |
| 6,733,905 B2 | 5/2004 | Takiguchi et al. | | 428/690 |
| 6,797,980 B2 | 9/2004 | Takiguchi et al. | | 257/40 |
| 6,808,827 B2 | 10/2004 | Igarashi et al. | | 428/690 |
| 6,812,497 B2 | 11/2004 | Kamatani et al. | | 257/79 |
| 6,821,645 B2 | 11/2004 | Igarashi et al. | | 428/690 |
| 6,824,894 B2 | 11/2004 | Takiguchi et al. | | 428/690 |
| 6,911,677 B2 | 6/2005 | Igarashi | | 257/98 |
| 7,037,598 B2 | 5/2006 | Igarashi | | 428/690 |
| 7,078,115 B2 | 7/2006 | Takiguchi et al. | | 428/690 |
| 7,108,924 B2 | 9/2006 | Kamatani et al. | | 428/690 |
| 7,238,437 B2 | 7/2007 | Igarashi et al. | | 428/690 |
| 7,279,233 B2 | 10/2007 | Tsuboyama et al. | | 428/690 |
| 7,306,856 B2 | 12/2007 | Igarashi et al. | | 428/690 |
| 7,329,898 B2 | 2/2008 | Igarashi | | 257/40 |
| 2004/0026663 A1* | 2/2004 | Heuer et al. | | 252/301.16 |
| 2005/0031904 A1 | 2/2005 | Igarashi et al. | | 428/690 |
| 2005/0079384 A1 | 4/2005 | Tsuboyama et al. | | 428/690 |
| 2006/0066225 A1 | 3/2006 | Kishino et al. | | 313/504 |
| 2006/0280968 A1 | 12/2006 | Kamatani et al. | | 428/690 |
| 2006/0286408 A1 | 12/2006 | Suzuki et al. | | 428/690 |
| 2007/0046177 A1 | 3/2007 | Furugori et al. | | 313/503 |
| 2007/0057250 A1 | 3/2007 | Takiguchi et al. | | 257/40 |
| 2007/0122652 A1 | 5/2007 | Hashimoto et al. | | 428/690 |
| 2007/0231602 A1 | 10/2007 | Igarashi et al. | | 428/690 |
| 2007/0232803 A1 | 10/2007 | Kamatani et al. | | 546/2 |
| 2007/0296671 A1* | 12/2007 | Han et al. | | 345/92 |
| 2008/0009627 A1 | 1/2008 | Tsuboyama et al. | | 546/139 |
| 2008/0116453 A1 | 5/2008 | Igarashi et al. | | 257/40 |

FOREIGN PATENT DOCUMENTS

| | | |
|---|---|---|
| EP | 1211257 | 6/2002 |
| JP | 2001/247859 | 9/2001 |
| JP | 2001/298470 | 4/2002 |
| JP | 2002/117978 | 4/2002 |
| JP | 2002/170684 | 6/2002 |
| JP | 2002/173674 | 6/2002 |
| JP | 2002/203679 | 7/2002 |
| JP | 2002/226495 | 8/2002 |
| JP | 2002/235076 | 8/2002 |
| JP | 2002/302671 | 10/2002 |
| JP | 2003/123982 | 4/2003 |
| JP | 2003/133074 | 5/2003 |
| WO | WO 0057676 | 9/2000 |
| WO | WO 0070655 | 11/2000 |
| WO | WO 0108230 | 2/2001 |
| WO | WO 0139234 | 5/2001 |
| WO | WO 0141512 | 6/2001 |
| WO | WO 02/02714 | 1/2002 |
| WO | WO 0215645 | 2/2002 |
| WO | WO 2006/059758 | 6/2006 |

OTHER PUBLICATIONS

O'Brien et al., "Improved Energy transfer in Electrophosphorescent Devices," *Appl. Phys. Lett.*, vol. 74, No. 3, 442-444 (1999).
Yamamoto, Akio, "Organic Metal, Base and Application," *Shokabo Publication Co., Ltd.*, pp. 150, 332 (1982) and translation.

Japan Society for the Promotion of Science, Organic Materials for Telecommunication Technology, 142nd commission, C meeting (Organic electronics), 9th research meeting document, items 25-32 (2005) and translation.
Thin Solid Films, 94 (1982) No. 2, 93-100, Vincett, et al.
Macromol. Symp. 125, 1 to 48 (1997) Chen, et al.
M.A. Baldo et al., "Very high-efficiency green organic light-emitting devices based on electrophosphorescence," Applied Physics Letters, vol. 75, No. 1, pp. 4-6 (1999).
H. Yersin, "Photochemistry and Photophysics of Coordination Compound," pp. 71-77 and 135-146, Springer-Verlag (1987).
Applied Physics Letters, vol. 79, pp. 2082-2084, Adachi, et al.
Nature, vol. 395, pp. 151-152, Baldo, et al.
Polymer Preprints, vol. 41, pp. 770-771 (2000), Djuorvich, et al.
Journal of American Chemical Society, vol. 123, pp. 4304-4312 (2001), Lamansky, et al.

\* cited by examiner

*Primary Examiner* — Jennifer Chriss
*Assistant Examiner* — Gregory Clark
(74) *Attorney, Agent, or Firm* — Fitzpatrick, Cella, Harper & Scinto

(57) ABSTRACT

Provided is an organic electroluminescent device which has a high efficiency and high durability. The organic electroluminescent device includes an anode and a cathode; and a layer including an organic compound interposed between the anode and the cathode, in which the layer includes a phosphorescent material including an Ir complex or Pt complex having at least one ligand represented by any one of the following general formulae (1) to (4):

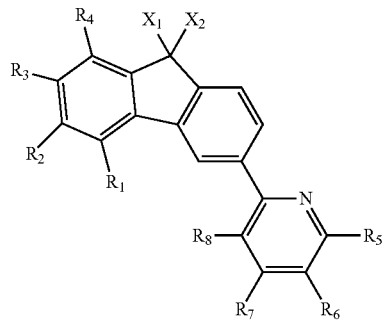

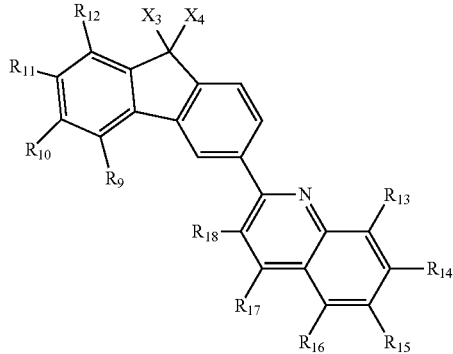

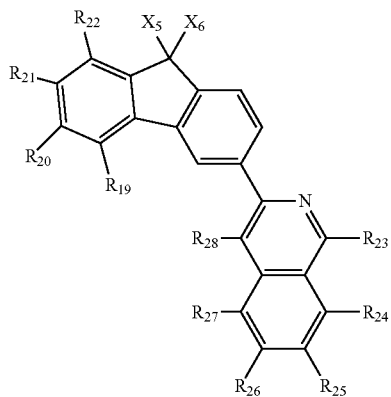

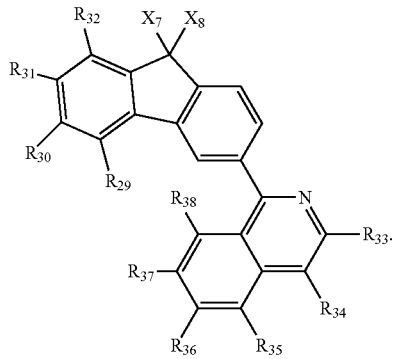

7 Claims, 4 Drawing Sheets

PHOSPHORESCENT MATERIAL, AND ORGANIC ELECTROLUMINESCENT DEVICE AND IMAGE DISPLAY APPARATUS USING SAME

BACKGROUND OF THE INVENTION

1. Field of the Invention

The present invention relates to a phosphorescent material, and an organic electroluminescent device and an image display apparatus using the phosphorescent material.

2. Description of the Related Art

In an old example of an electroluminescent device, a voltage has been applied to an anthracene evaporated film to emit light (Thin Solid Films, 94, 171 (1982)). In recent years, it has been known that the area of the organic electroluminescent device among electroluminescent devices can be increased more easily than the inorganic electroluminescent device and a novel material of the organic electroluminescent device can be easily developed to provide desired color development by using the material or a combination thereof. Further, as the organic electroluminescent device has advantages including its ability to be driven at a low voltage, application research has been vigorously conducted on the transformation of an organic electroluminescent device as an electroluminescent device having high-speed responsivity and high efficiency into a device including the development of a material for the device.

For example, Macromol. Symp. 125, 1 to 48 (1997) discusses an organic electroluminescent device in which two upper and lower layers of electrodes and an organic layer including a light-emitting layer between the electrodes are formed on a transparent substrate.

Meanwhile, in recent years, investigation has been conducted on not only a conventional system utilizing fluorescence upon transition from an excited singlet exciton to a ground state but also a system utilizing phosphorescence via an excited triplet exciton. Specific examples of an organic electroluminescent device using phosphorescence is described in each of "Improved energy transfer in electrophosphorescent device" (D. F. O'Brien et al., Applied Physics Letters Vol. 74, No. 3, p. 422 (1999)) and "Very high-efficiency green organic light-emitting devices based on electrophosphorescence" (M. A. Baldo et al., Applied Physics Letters Vol. 75, No. 1, p. 4 (1999)). In each of those documents, an organic layer having a four-layer structure has been mainly used. Such a four-layer structure includes, for example, a hole-transporting layer, a light-emitting layer, an exciton diffusion-prevention layer, and an electron-transporting layer disposed in the named order from an anode side. Further, as a phosphorescent material contained in the organic electroluminescent device having such a structure, $Ir(ppy)_3$ is widely known.

As described above, an organic electroluminescent device has recently showed significant progress. The organic electroluminescent device is characterized in that it has a high luminance at a low applied voltage, a variety of emission wavelengths, and a high-speed responsivity and can be subjected to thickness reduction and weight reduction. The characteristic suggests the potential of the organic electroluminescent device to find use in a wide variety of applications.

However in terms of practical use, at present, an optical output with a higher luminance, or a high conversion efficiency has been demanded. In addition, there still remain a large number of problems in terms of durability such as a time-dependent change due to long-term use and degradation due to an atmospheric gas containing oxygen or due to moisture. Further, good color purity and a red emission with a high efficiency are demanded when the application of the device to a full-color display or the like is taken into consideration. However, it cannot be said that those problems have been satisfactorily solved.

SUMMARY OF THE INVENTION

It is, therefore, an object of the present invention to provide a novel phosphorescent material. Further, it is another object of the present invention to provide an organic electroluminescent device having a high efficiency and high durability.

The above objects can be achieved by using the phosphorescent material according to the present invention. That is, the phosphorescent material according to the present invention is an Ir complex or a Pt complex having at least one ligand represented by any one of the following general formulae (1) to (4):

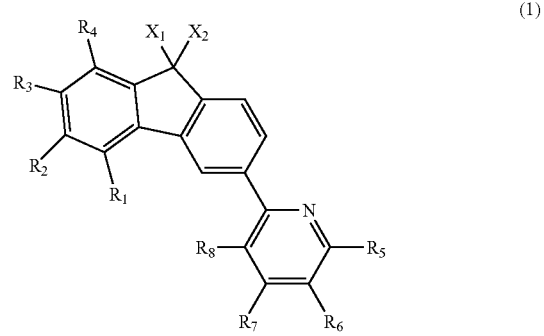

(1)

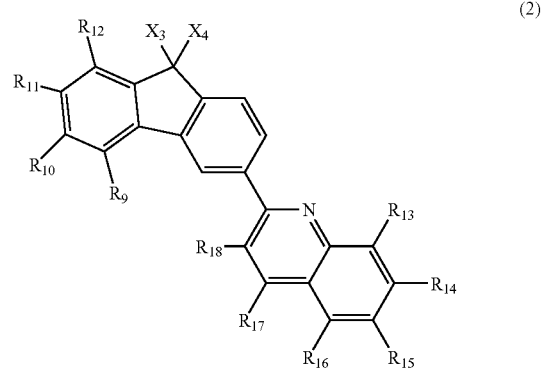

(2)

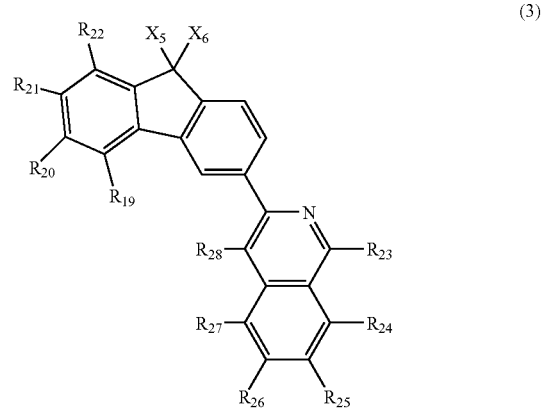

(3)

-continued

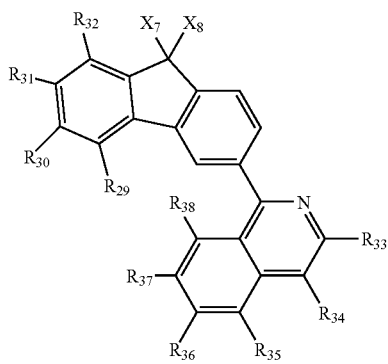

(4)

invention is an Ir complex or a Pt complex having at least one ligand represented by any one of the following general formulae (1) to (4).

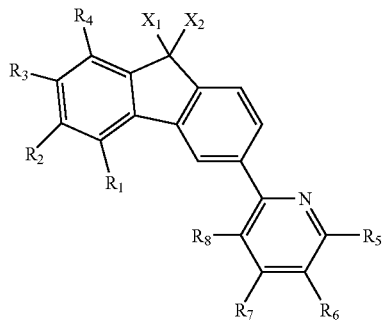

(1)

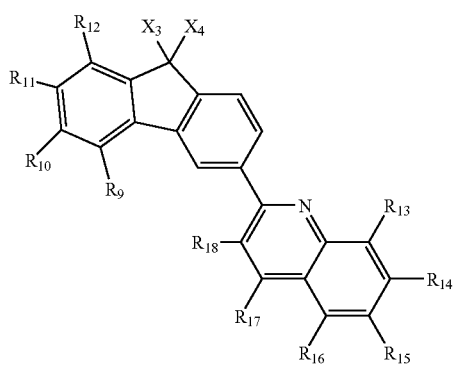

(2)

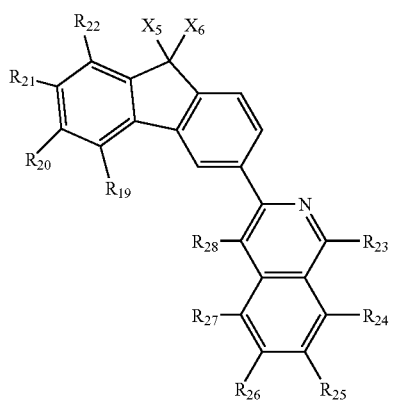

(3)

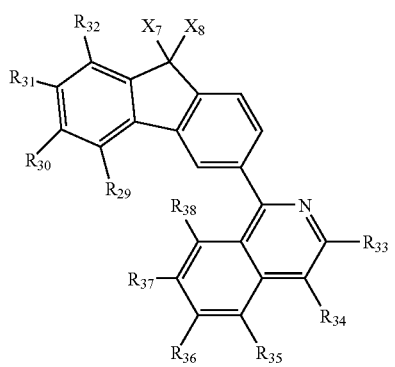

(4)

wherein in the formula (1), either one of $X_1$ and $X_2$ is a fluorinated alkyl group having 1 to 20 carbon atoms, and another of $X_1$ and $X_2$, which is not a fluorinated alkyl group having 1 to 20 carbon atoms, is an aryl group or an alkyl group; in the formula (2), either one of $X_3$ and $X_4$ is a fluorinated alkyl group having 1 to 20 carbon atoms, and another of $X_3$ and $X_4$, which is not a fluorinated alkyl group having 1 to 20 carbon atoms, is an aryl group or an alkyl group; in the formula (3), either one of $X_5$ and $X_6$ is a fluorinated alkyl group having 1 to 20 carbon atoms, and another of $X_5$ and $X_6$, which is not a fluorinated alkyl group having 1 to 20 carbon atoms, is an aryl group or an alkyl group; in the formula (4), either one of $X_7$ and $X_8$ is a fluorinated alkyl group having 1 to 20 carbon atoms, and another of $X_7$ and $X_8$, which is not a fluorinated alkyl group having 1 to 20 carbon atoms, is an aryl group or an alkyl group; and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, and $R_{32}$ each represent, independently of one another, a hydrogen atom, a halogen atom, or an alkyl group having 1 to 20 carbon atoms.

According to the present invention, a novel phosphorescent material can be provided. Further, according to the present invention, an organic electroluminescent device having a high efficiency and high durability can be provided.

Further features of the present invention will become apparent from the following description of exemplary embodiments with reference to the attached drawings.

DESCRIPTION OF THE EMBODIMENTS

Figure 1:
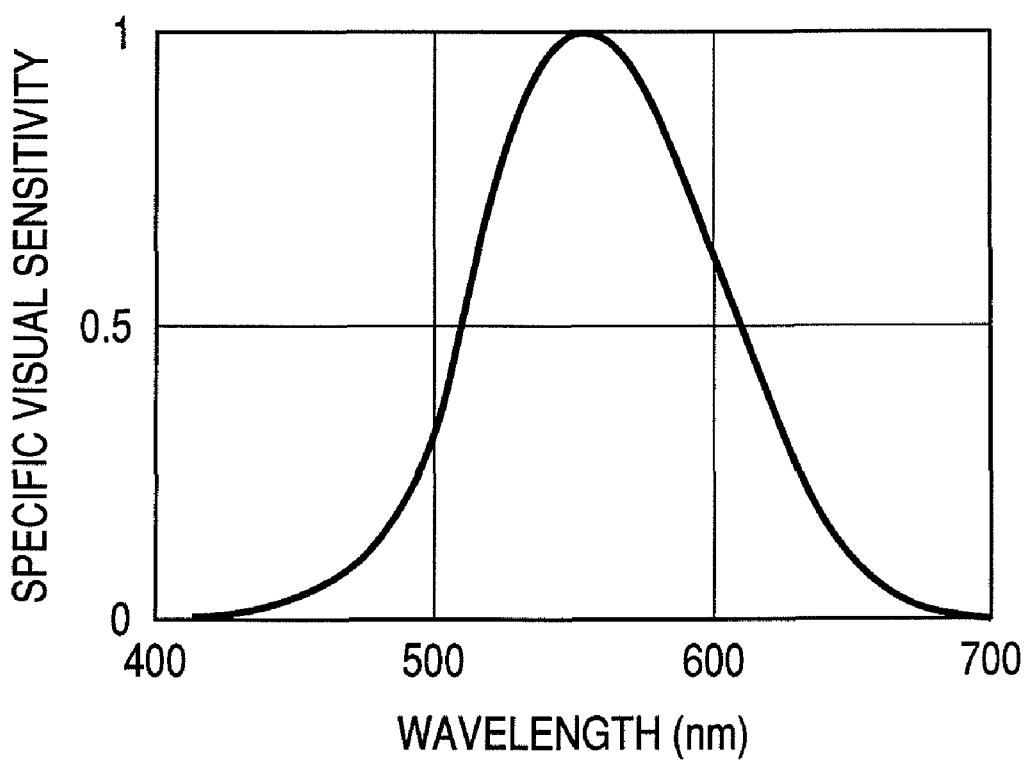
FIG. 1 is a graphical representation illustrating a specific visual sensitivity curve.

First, the phosphorescent material of the present invention will be described. The phosphorescent material of the present invention is an Ir complex or a Pt complex having at least one ligand represented by any one of the following general formulae (1) to (4).

In the formula (1), either one of $X_1$ and $X_2$ is a fluorinated alkyl group having 1 to 20 carbon atoms.

In the formula (2), either one of $X_3$ and $X_4$ is a fluorinated alkyl group having 1 to 20 carbon atoms.

In the formula (3), either one of $X_5$ and $X_6$ is a fluorinated alkyl group having 1 to 20 carbon atoms.

In the formula (4), either one of $X_7$ and $X_8$ is a fluorinated alkyl group having 1 to 20 carbon atoms.

The fluorinated alkyl group having 1 to 20 carbon atoms represented by $X_1$ to $X_8$ is a substituent selected from the following (a) and (b).

(a) A substituent in which all the hydrogen atoms contained in an alkyl group is replaced by fluorine atoms.

(b) A substituent in which a part of hydrogen atoms contained in an alkyl group is replaced by fluorine atom(s), and all or a part of the remaining hydrogen atom(s) is replaced by halogen atom(s) other than fluorine, such as bromine, iodine, and chlorine, or deuterium atom.

Specific examples of the above alkyl groups include a methyl group, an ethyl group, an n-propyl group, an n-butyl group, an n-hexyl group, an n-octyl group, an isopropyl group, an isobutyl group, a tertiary butyl group, a cyclohexyl group, and a cyclopentyl group.

In the formula (1), of $X_1$ and $X_2$, one being not a fluorinated alkyl group having 1 to 20 carbon atoms is an aryl group or an alkyl group.

In the formula (2), of $X_3$ and $X_4$, one being not a fluorinated alkyl group having 1 to 20 carbon atoms is an aryl group or an alkyl group.

In the formula (3), of $X_5$ and $X_6$, one being not a fluorinated alkyl group having 1 to 20 carbon atoms is an aryl group or an alkyl group.

In the formula (4), of $X_7$ and $X_8$, one being not a fluorinated alkyl group having 1 to 20 carbon atoms is an aryl group or an alkyl group.

Specific examples of the above alkyl groups include a methyl group, an ethyl group, an n-propyl group, an n-butyl group, an n-hexyl group, an n-octyl group, an isopropyl group, an isobutyl group, a tertiary butyl group, a cyclohexyl group, a cyclopentyl group, and a cyclopropyl group.

Specific examples of the above aryl groups include a phenyl group, a tolyl group, a xylyl group, a naphthyl group, a methylnaphthyl group, an anthryl group, a phenanthryl group, and a biphenyl group.

In the formulae (1) to (4), $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, and $R_{32}$ each represent, independently of one another, a hydrogen atom, a halogen atom, or an alkyl group having 1 to 20 carbon atoms.

Examples of the halogen atoms represented by $R_1$ to $R_{32}$ include fluorine, chlorine, bromine, and iodine.

Examples of the alkyl group having 1 to 20 carbon atoms represented by $R_1$ to $R_{32}$ include an ethyl group, an n-propyl group, an n-butyl group, an n-hexyl group, an n-octyl group, an isopropyl group, an isobutyl group, a tertiary butyl group, a cyclohexyl group, and a cyclopentyl group. All or a part of the hydrogen atoms in the above alkyl groups may be replaced by fluorine atoms.

The phosphorescent material of the present invention is an organic metal complex containing Ir or Pt as a central metal. When this central metal is represented by M, the organic metal complex that is the phosphorescent material of the present invention can be represented by the following general formula (5):

$$ML_mL'_n \tag{5}$$

In the general formula (5), m represents an integer of 1 to 3, and n represents an integer of 0 to 2, provided that m+n represents 2 or 3.

In the general formula (5), L represents any one of the ligands represented by the general formulae (1) to (4).

In the general formula (5), L' represents any one of the ligands represented by the following general formulae (6) to (8).

In the general formula (6), A represents a benzene ring, a monocyclic heterocyclic ring, or a fused ring.

When A is a monocyclic heterocyclic ring, specific examples thereof include a thiophene ring, a furan ring, an imidazole ring, an oxazole ring, a pyrrole ring, a thiazole ring, a pyrazole ring, a pyridine ring, a pyridazine ring, a pyrazine ring, a morpholine ring, a 2H-pyran ring, and a 4H-pyran ring.

When A is a fused ring, specific examples thereof include a carbazole ring, a fluorenyl group, a dibenzothiophene ring, a dibenzofuran ring, a phenothiazine ring, and a phenoxazine ring.

The benzene ring, the monocyclic heterocyclic ring, or the fused ring represented by A may further include a substituent. Examples of the substituent include fluorine and a phenyl group.

In the general formula (6), B represents a heterocyclic ring containing a nitrogen atom. Specific examples of such a heterocyclic ring include a pyridine ring, a pyridazine ring, a pyrimidine ring, a pyrazine ring, a quinoxaline ring, a quinoline ring, a naphthylidine ring, a pyrrole ring, an imidazole ring, a thiazole ring, and a pyrazole ring.

In the general formula (6), A and B are covalently bonded to each other.

In the general formula (7), B' represents a heterocyclic ring containing a nitrogen atom. Specific examples of the heterocyclic ring include a pyridine ring, a pyridazine ring, a pyrimidine ring, a pyrazine ring, a quinoxaline ring, a quinoline ring, a naphthylidine ring, a pyrrole ring, an imidazole ring, a thiazole ring, and a pyrazole ring.

In the general formula (8), E and G each represent a linear or branched alkyl group having 1 to 20 carbon atoms or a substituted or unsubstituted aryl group.

When E or G is an alkyl group, specific examples thereof include a methyl group, an ethyl group, an n-propyl group, an n-butyl group, an n-hexyl group, an n-octyl group, an isopropyl group, an isobutyl group, and a tertiary butyl group. At this time, all or a part of the hydrogen atoms contained in the alkyl group may be substituted with fluorine atom(s).

When E or G is an aryl group, specific examples thereof include a phenyl group, a tolyl group, a xylyl group, a naphthyl group, a methylnaphthyl group, an anthryl group, a phenanthryl group, a biphenyl group, a terphenyl group, and a fluorenyl group. Examples of a substituent which the aryl group may have include: halogen atoms such as a fluorine atom, a chlorine atom, a bromine atom, and an iodine atom; and a cyano group.

In the general formula (8), J represents a halogen atom such as a fluorine atom, a chlorine atom, a bromine atom, or an iodine atom, a linear or branched alkyl group having 1 to 20 carbon atoms, or a substituted or unsubstituted aryl group.

When J is an alkyl group, specific examples thereof include a methyl group, an ethyl group, an n-propyl group, an n-butyl group, an n-hexyl group, an n-octyl group, an isopropyl group, an isobutyl group, and a tertiary butyl group. In this case, the hydrogen atom(s) contained in the alkyl group may be substituted with fluorine atom(s).

When is an aryl group, specific examples thereof include a phenyl group, a tolyl group, a xylyl group, a naphthyl group, a methylnaphthyl group, an anthryl group, a phenanthryl group, a biphenyl group, a terphenyl group, and a fluorenyl group. Examples of a substituent which the aryl group may have include: halogen atoms such as a fluorine atom, a chlorine atom, a bromine atom, and an iodine atom; and a cyano group.

The phosphorescent material of the present invention is an Ir complex or Pt complex having any one of the ligands represented by the general formulae (1) to (4). The ligands of the general formulae (1) to (4) have a fluorinated alkyl group at the 9-position or the 9'-position of a fluorene skeleton. In this case, the phosphorescent material may have a fluorinated alkyl group at each of the 9- and the 9'-positions of the fluorene skeleton.

When a compound having a fluorinated alkyl group at the 9-position or the 9'-position of a fluorene skeleton is introduced as a ligand constituting a complex, there are exhibited the following advantages.

1. The phosphorescent material exhibits excellent solubility with respect to various kinds of solvents.
2. The emission color of the phosphorescent material can be controlled, and a phosphorescent material having satisfactory color purity can be obtained.
3. The electron acceptability of the complex is improved, and the emission quantum efficiency is improved.
4. The carrier transportability of the complex is improved, and the light emission efficiency of an organic electroluminescent device is improved.

Hereinafter, the principle and reasons for the above advantages will be described.

The first advantage can be obtained as follows. The localization of electrons in molecules serving as ligands is controlled by fluorine atoms having high electronegativities, whereby the intermolecular force between complex molecules serving as a phosphorescent material is weakened, so that the molecules become difficult to be crystallized. Further, due to the introduction of fluorine atoms, the polarity of the complex itself is increased, so that the complex becomes easy to be dissolved in a solvent having a high polarity.

The reason for the exhibition of the second advantage is considered as follows. The ligands of the general formulae (1) to (4) each have a donor-acceptor structure in which a fluorene skeleton moiety having an electron donating property (donative property) is bonded to a pyridine, quinoline, or isoquinoline skeleton moiety having an electron-deficient property (acceptive property). In the ligands of the general formulae (1) to (4), a fluorinated alkyl group that is an electron attractive group is further introduced into a fluorene skeleton that is a donative moiety. From this, if the acceptor moiety is the same, the emission wavelength of the complex can be shifted to blue, compared with one that does not basically have an electron attractive group.

If this function is utilized, the emission wavelength of light emission by a complex can be controlled freely. More specifically, even in the case where the emission wavelength of a complex is shifted to red due to the substituent effect of the acceptor moiety, the emission wavelength can be returned to an arbitrary emission wavelength by utilizing a substituent effect on the donative moiety side as shown below.

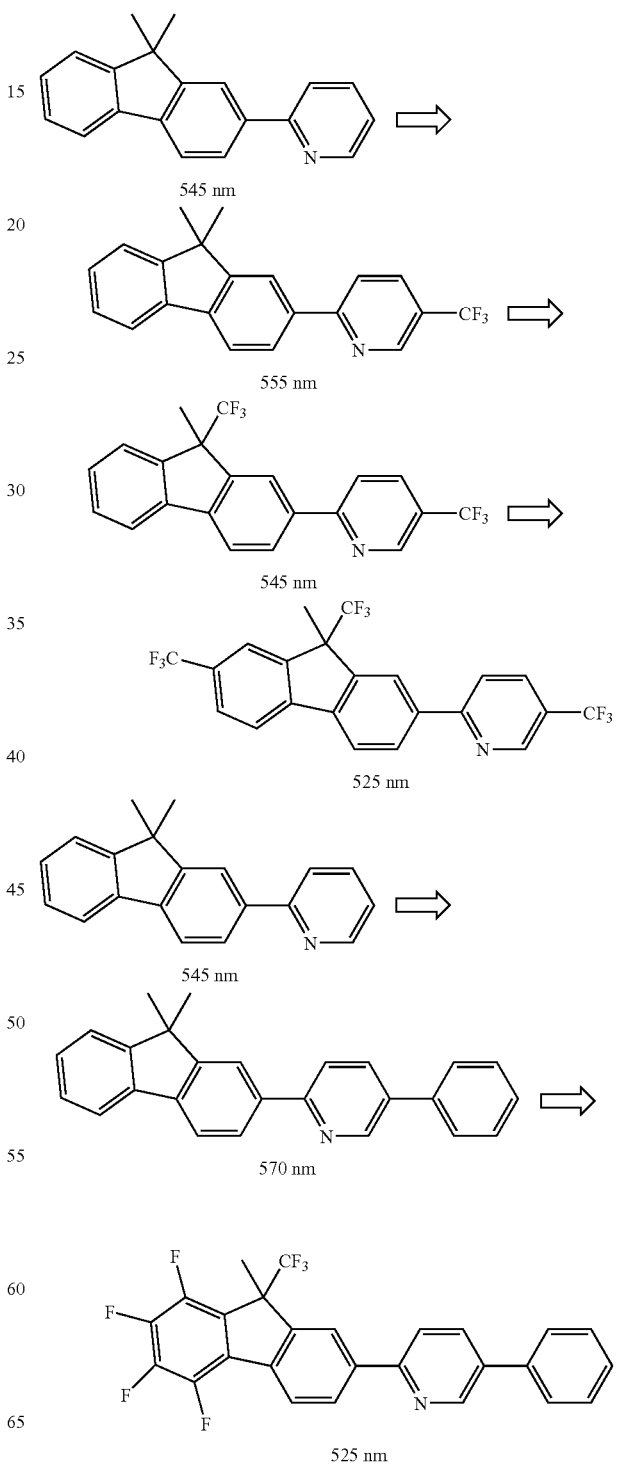

Therefore, regardless of what substituent is introduced into an acceptive moiety, a preferred red, green, or blue emission wavelength can be obtained, by utilizing the magnitude of the electron-withdrawing property of the donative moiety. Incidentally, the term "emission wavelength" herein employed means an emission wavelength obtained from an organic electroluminescent device. That is, it refers to an emission wavelength which is a red, green, or blue emission wavelength according to NTSC chromaticity coordinates or HDTV chromaticity coordinates considered being an index of high color purity and is an emission wavelength having a higher range of visual sensitivity. For example, a red color is about 605 to 780 nm in a visible light region. However, a red color of 640 nm or more is felt to be very dark due to the influence of visual sensitivity. This is apparent also from a specific visual sensitivity curve illustrated in FIG. 1. Therefore, a desired red emission wavelength is 605 to 640 nm that is a red wavelength having a high color purity and high visual sensitivity. On the other hand, a desired green emission wavelength is 500 to 540 nm, and a desired blue emission wavelength is 430 to 460 nm. Therefore, they are each within a very narrow range.

The third advantage is exhibited as follows. That is, the LUMO (lowest unoccupied molecular orbital) level of the entire ligand is enhanced by introducing a fluorinated alkyl group. Because of this, the electron acceptability of the entire complex is also enhanced, and regarding the emission form of the complex, the $^3$MLCT (Metal to Ligand Charge Transfer Transition) property becomes stronger rather than the $^3\pi\text{-}\pi^*$ property. Consequently, there is a large possibility that a complex having large emission energy dependency of a radiation rate constant kr, i.e., a complex with a high emission yield may be obtained.

The fourth advantage is that a ring (an aryl group or a heterocyclic group) saturated with fluorine atoms having high electronegativity becomes an electron deficient state and is likely to receive electrons. For example, the following fluorinated aryl group or fluorinated heterocyclic group:

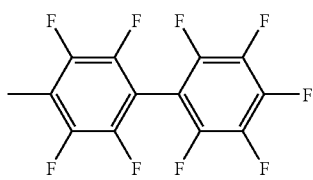
B1

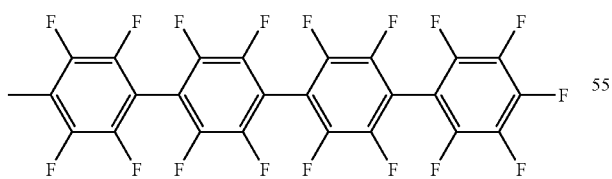
B2

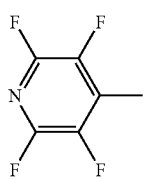
B3

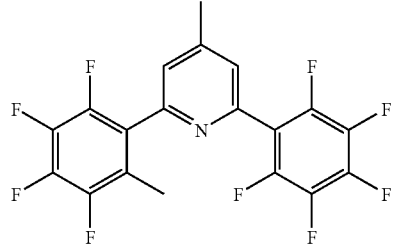
B4 functions as a carrier transporting moiety (in particular, an electron transporting moiety) due to the above effect. The phosphorescent material of the present invention has also a fluorinated alkyl group introduced into the 9-positon or the 9'-position of a fluorene skeleton in a ligand, so that the fluorene skeleton functions as a carrier transporting moiety (in particular, an electron transporting moiety).

Hereinafter, although specific examples of the phosphorescent material of the present invention will be enumerated, the present invention is not limited thereto.

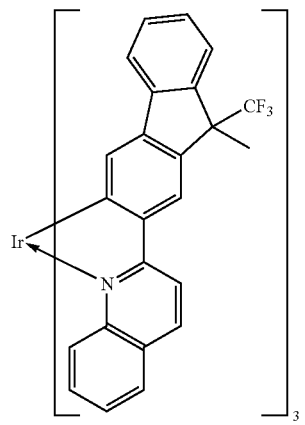
C1

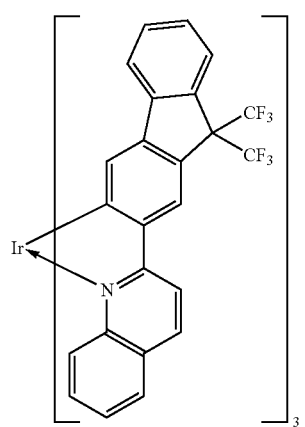
C2

C3
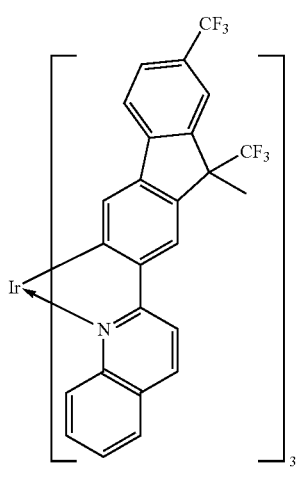
C4
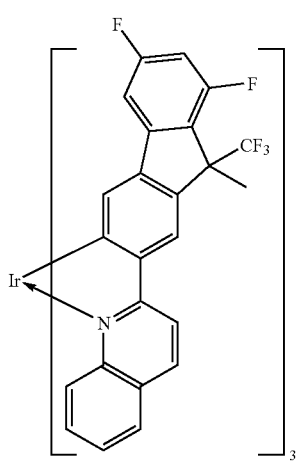
C5
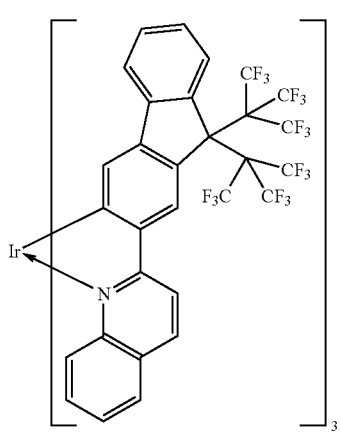
C6
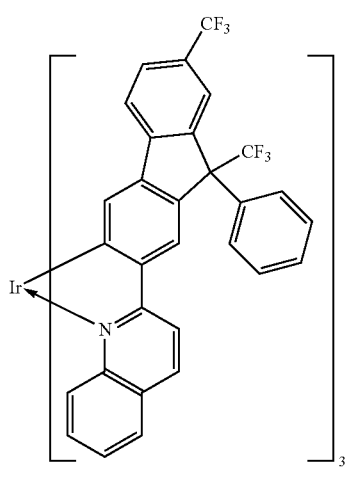
C7
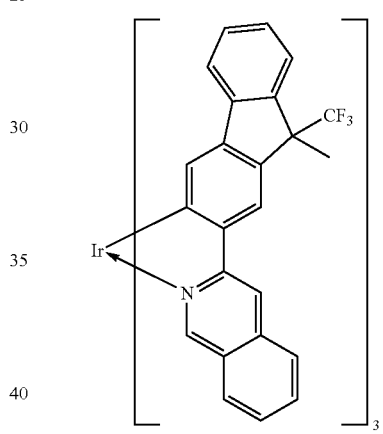
C8
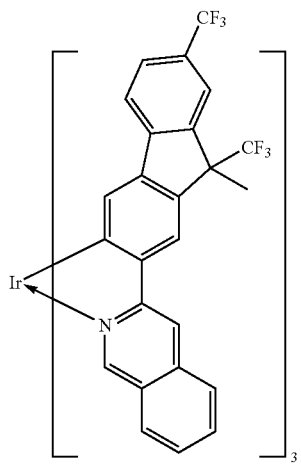

C9
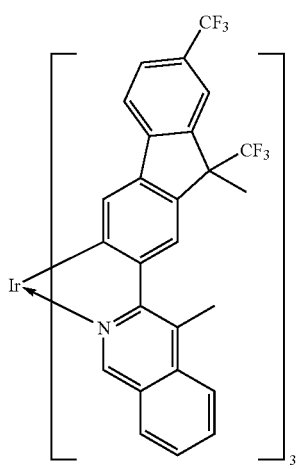
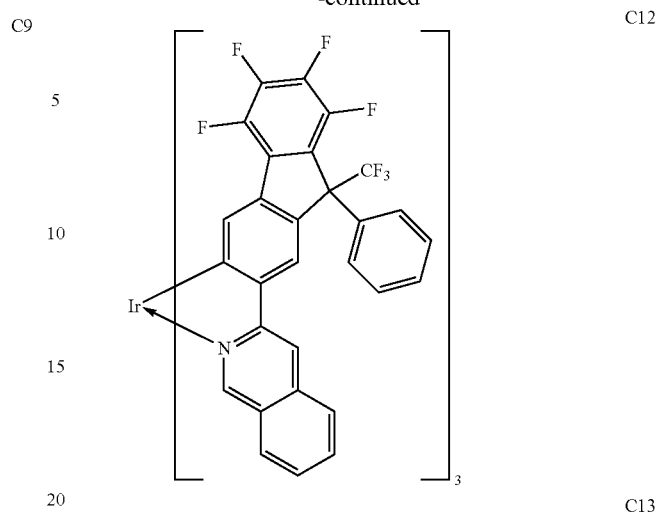 C12
C10
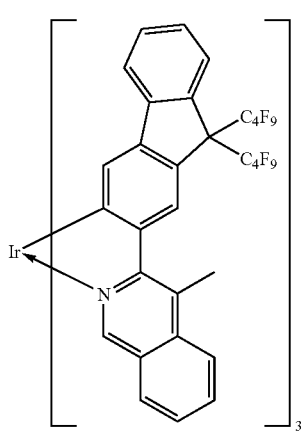
C13
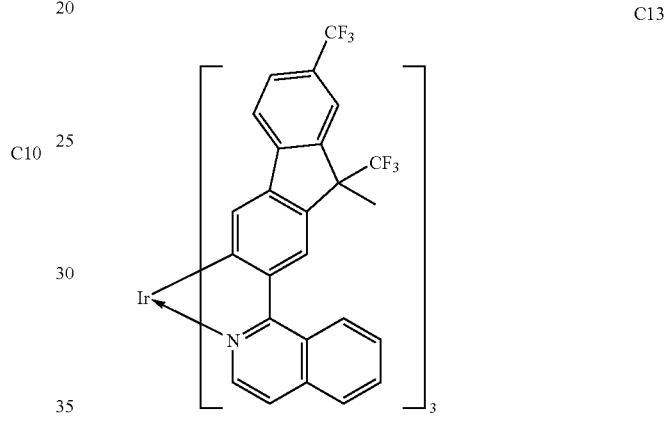
C14
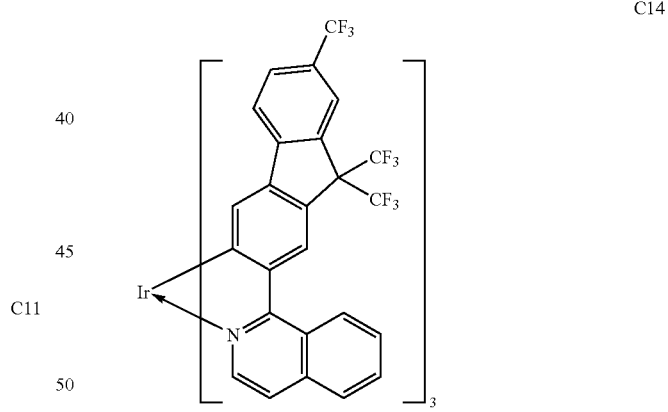
C11
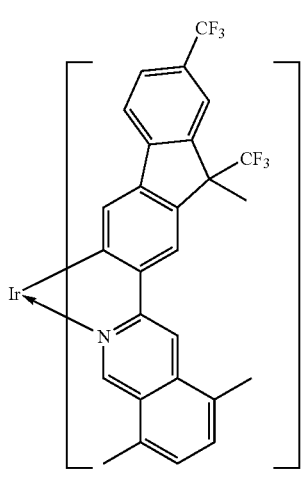
C15
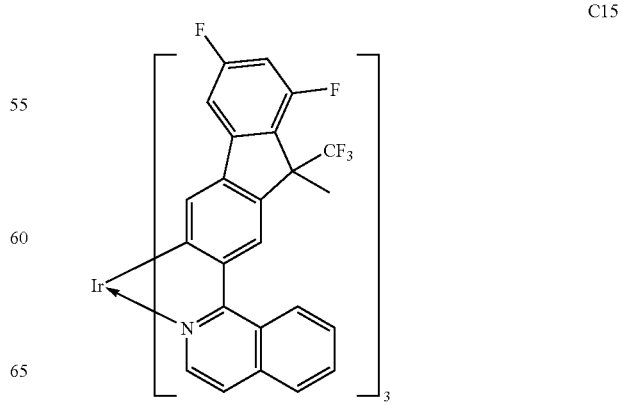

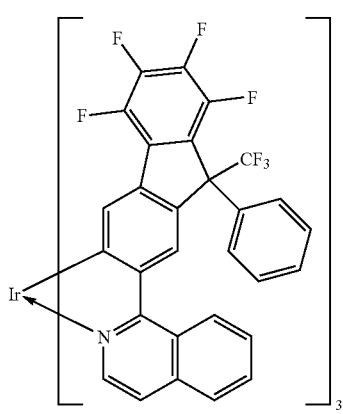
C16
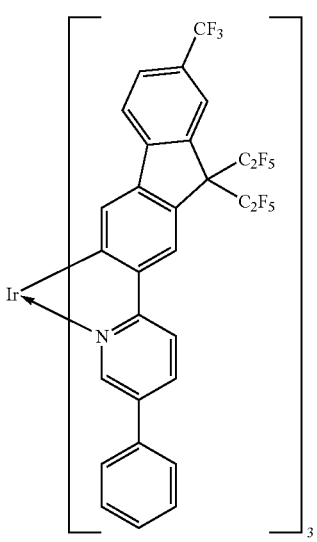
C19
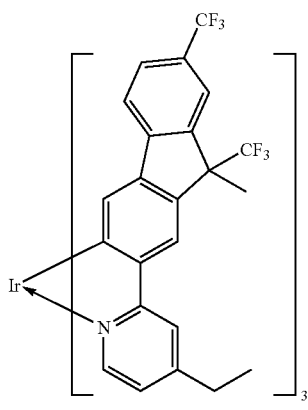
C17
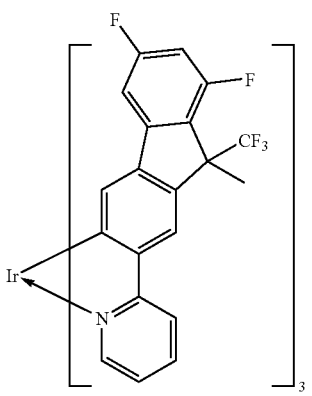
C20
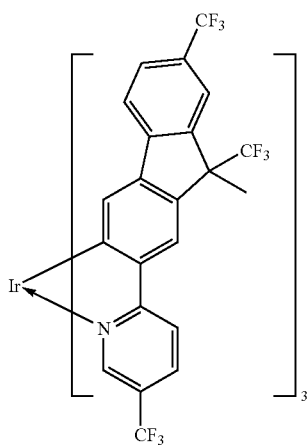
C18
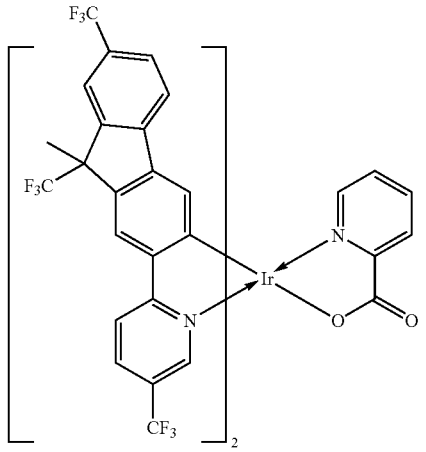
C21

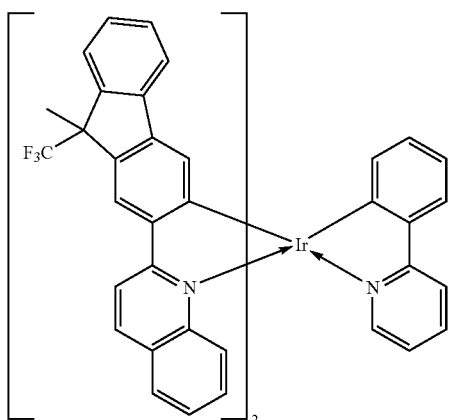
C22
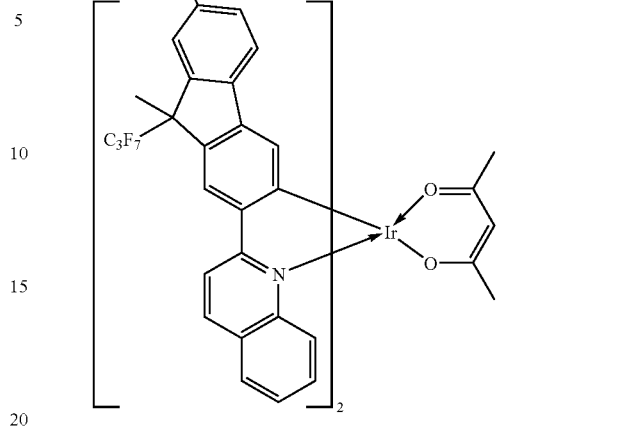
C25
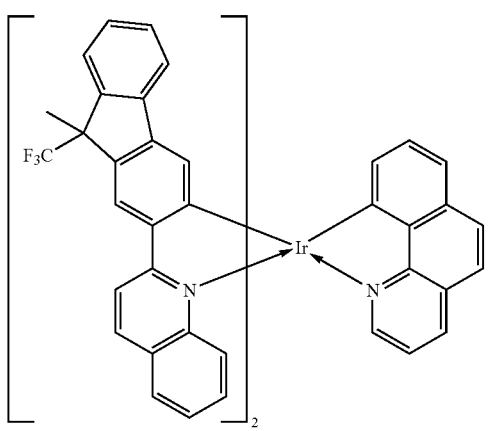
C23
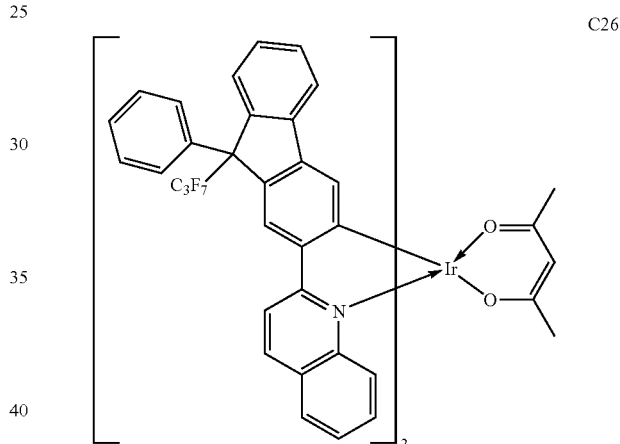
C26
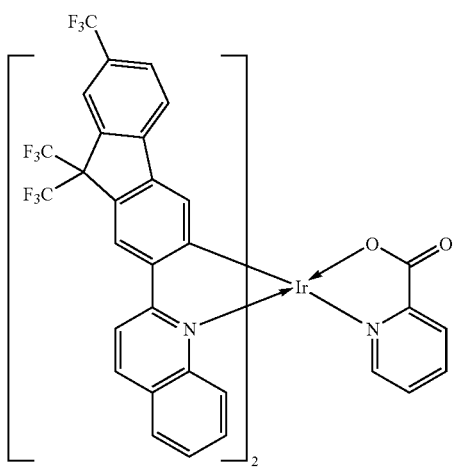
C24
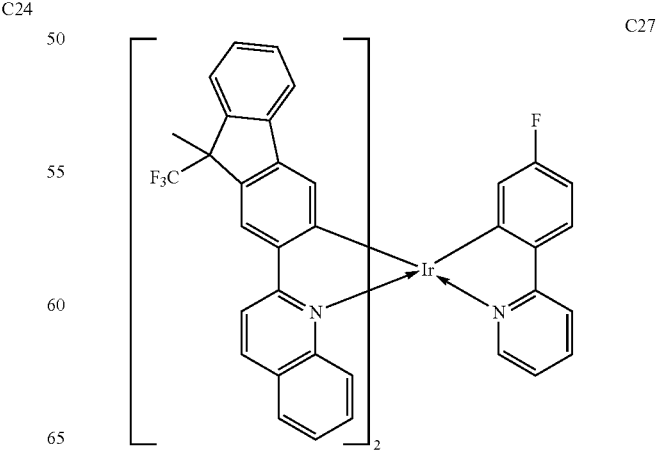
C27

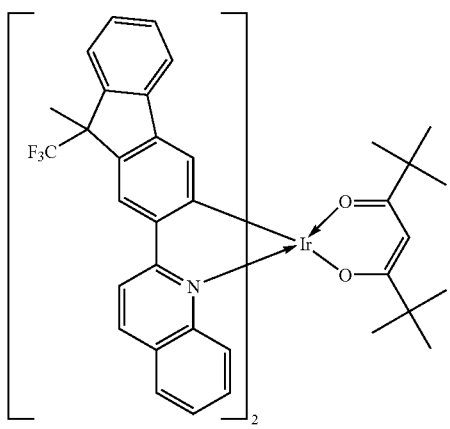
C28
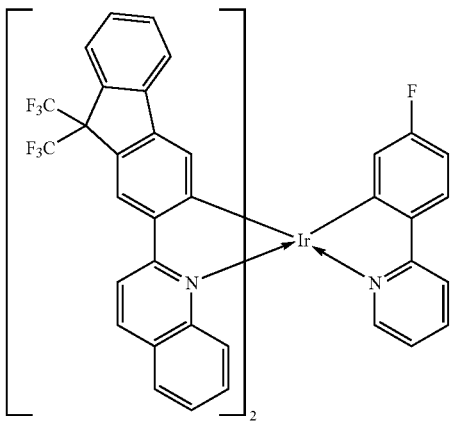
C31
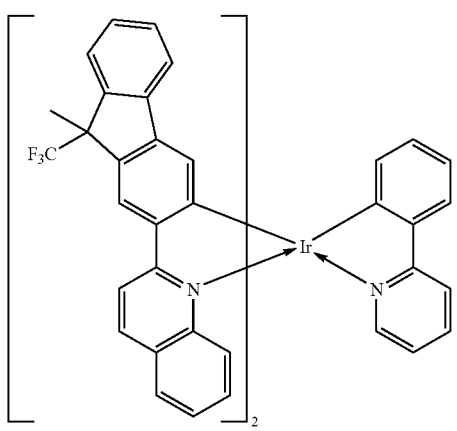
C29
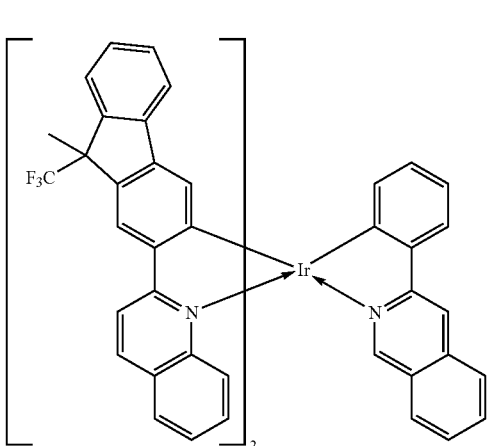
C32
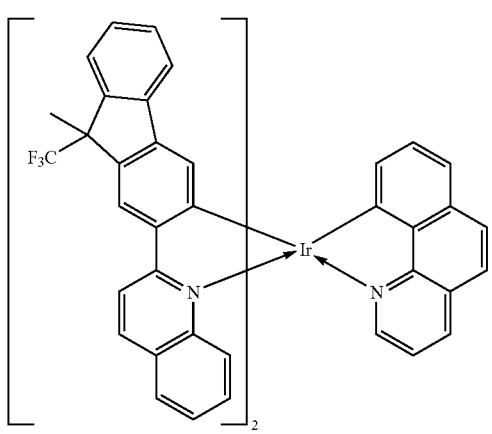
C30
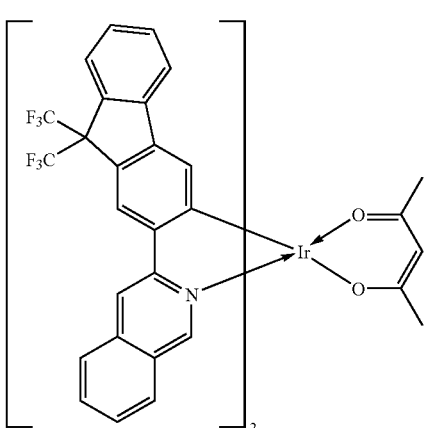
C33

-continued
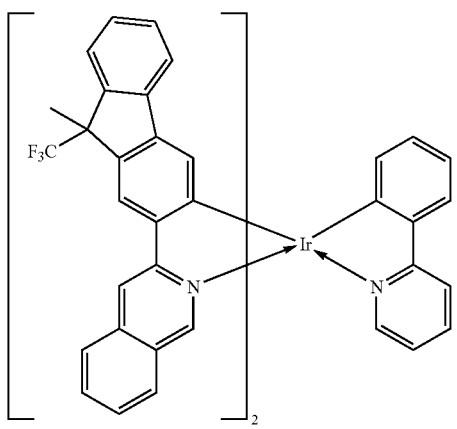 C34
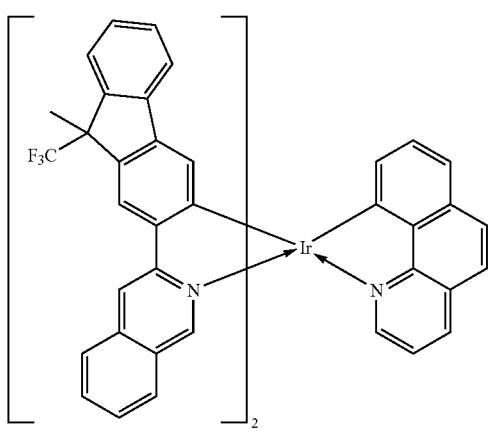 C35
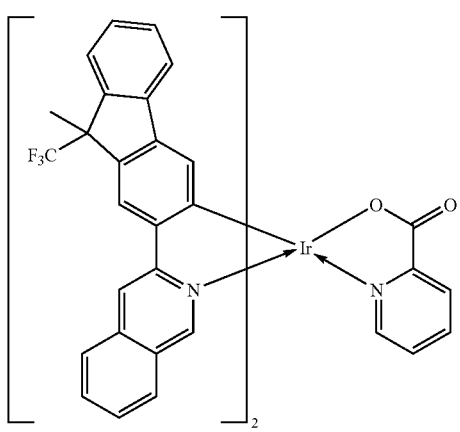 C36
-continued
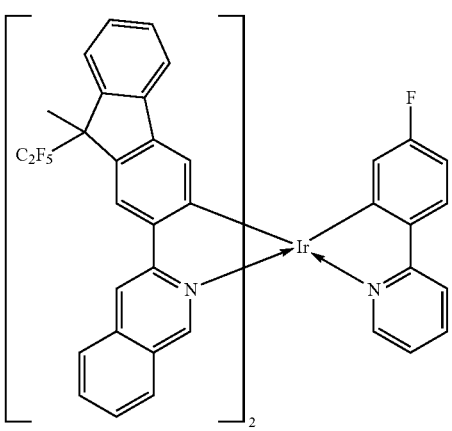 C37
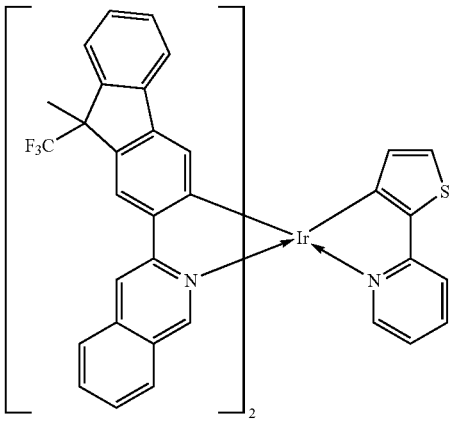 C38
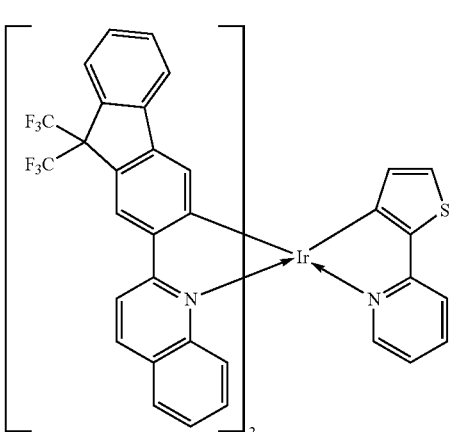 C39

C40
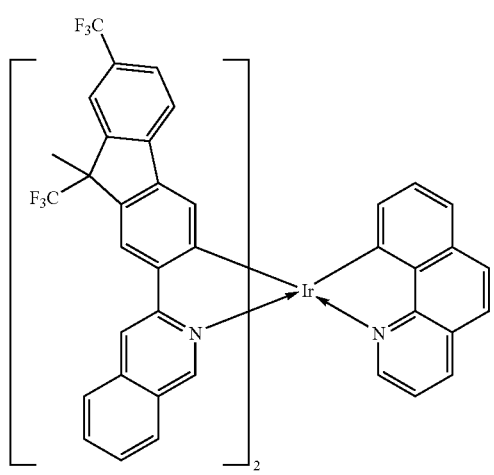
C41
C42
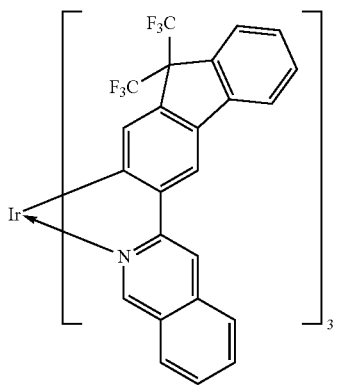
C43
C44
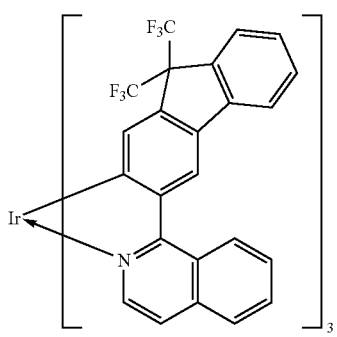
C45
C46
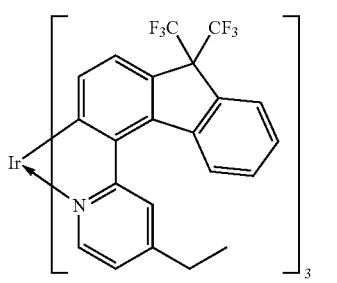
C47
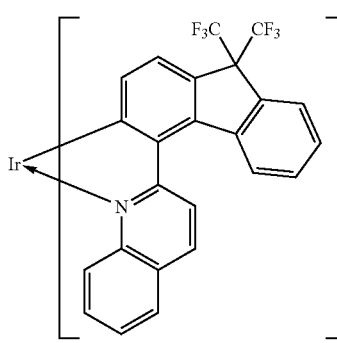

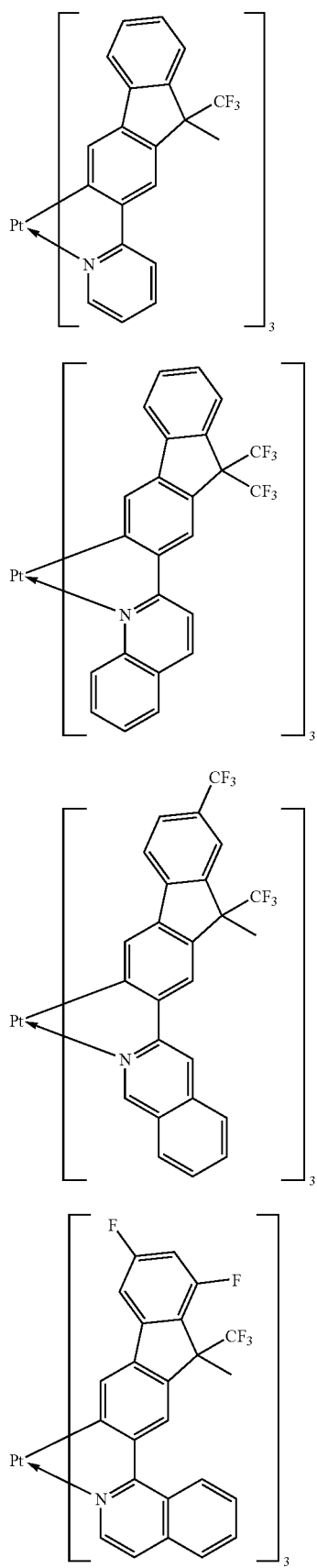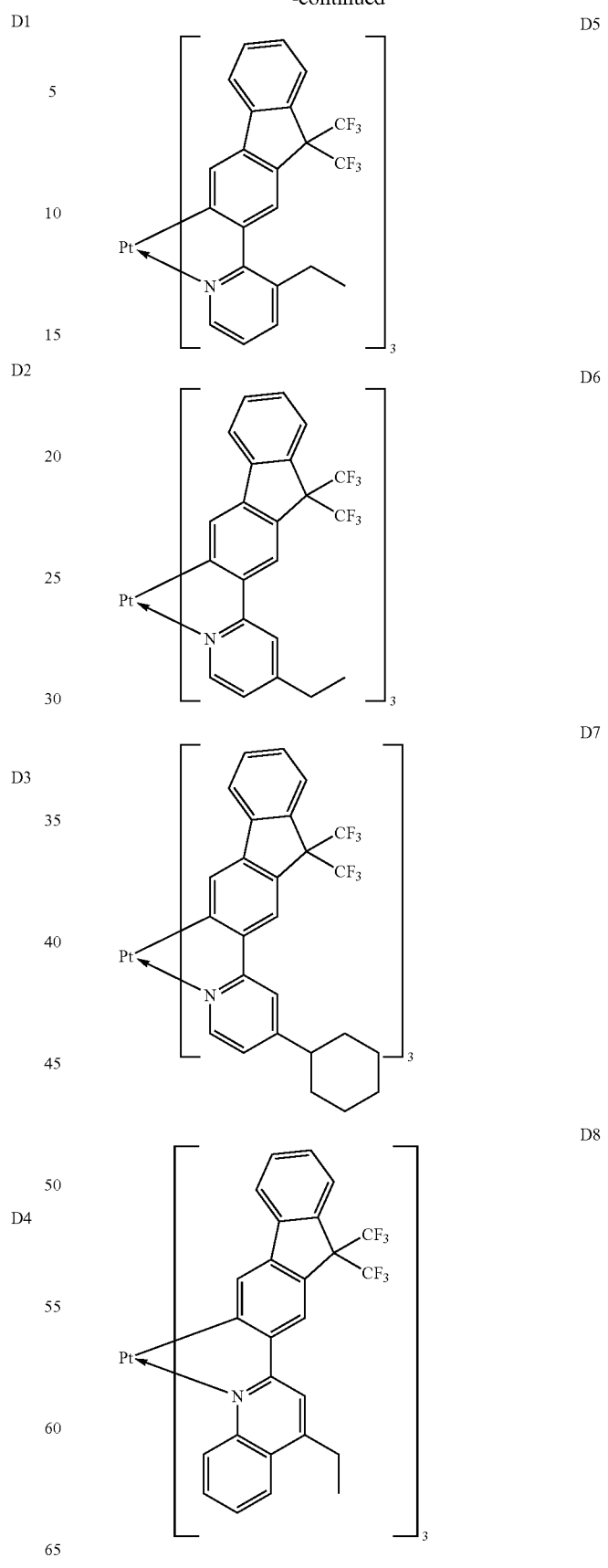

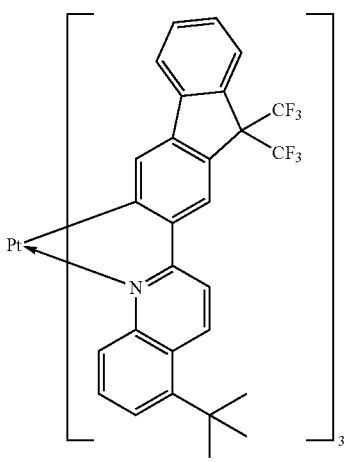

$$\Bigg]_3 \quad D9$$

Next, the organic electroluminescent device of the present invention will be described. The organic electroluminescent device of the present invention includes an anode, a cathode, and a layer formed of an organic compound, the layer being interposed between the anode and the cathode.

Hereinafter, the organic electroluminescent device of the present invention will be described in detail with reference to the accompanying drawings.

In FIGS. 2A, 2B, 2C, 3, 4, and 5, reference numerals 1a, 1b, 1c, and 34 each denote an organic electroluminescent device; 11, a metal electrode; 12, a light-emitting layer; 13, a hole-transporting layer; 14, a transparent electrode; 15, a transparent substrate; 16, an electron-transporting layer; 17, an exciton diffusion-prevention layer; 20 and 40, an image display apparatus; 21, a scanning signal driver; 22, an information signal driver; 23, a current supply source; 30, a pixel circuit; 31, a first thin film transistor (TFT); 32, a capacitor; 33, a second thin film transistor (TFT); 41, a substrate; 42, a moisture-resistant film; 43, a gate electrode; 44, a gate insulating film; 45, a semiconductor layer; 46, a drain electrode; 47, a source electrode; 48, a TFT element; 49, an insulating film; 50, a contact hole (through-hole); 51, an anode; 52, an organic layer; 53, a cathode; 54, a first protective layer; and 55, a second protective layer.

Figure 2A:
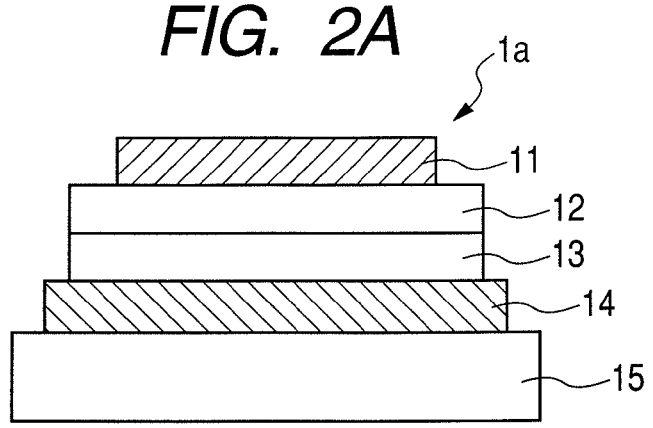
FIGS. 2A, 2B, and 2C are cross-sectional views illustrating first, second, and third exemplary embodiments of an organic electroluminescent device of the present invention.
Figure 2B:
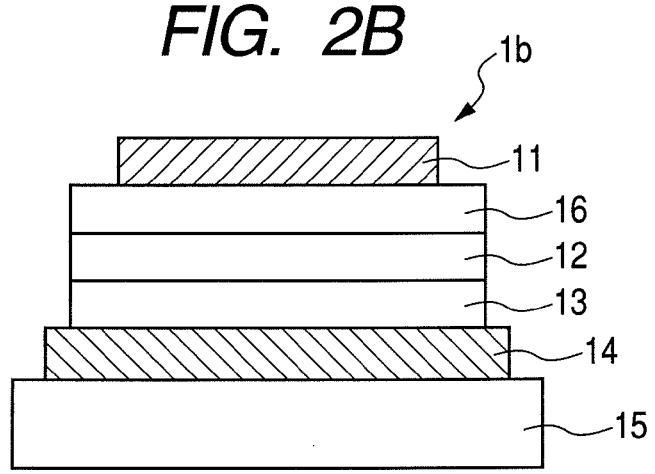
Figure 2C:
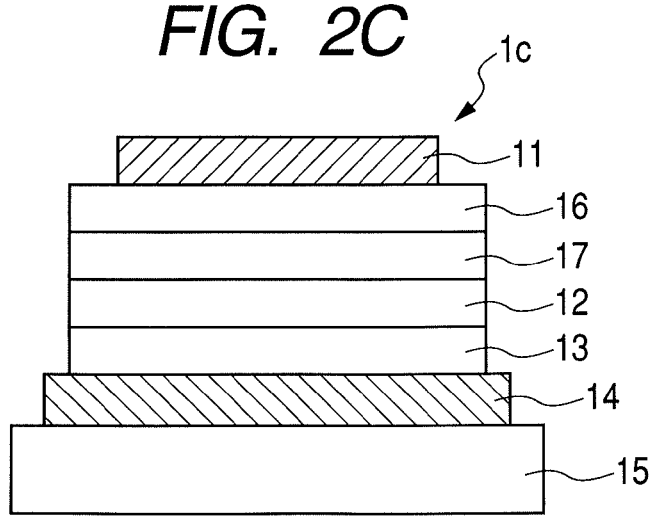

FIGS. 2A to 2C are cross-sectional views each illustrating an example of an embodiment of an organic electroluminescent device of the present invention. Herein, FIG. 2A refers to a first embodiment, FIG. 2B refers to a second embodiment, and FIG. 2C refers to a third embodiment, respectively.

In an organic electroluminescent device 1a shown in FIG. 2A, a stack in which the metal electrode 11, the light-emitting layer 12, the hole-transporting layer 13, and the transparent electrode 14 are disposed in the stated order from above is provided on the transparent substrate 15.

In general, the organic electroluminescent device has a structure in which the transparent electrode 14 having a film thickness of 50 to 200 nm, a layer containing a plurality of organic compounds, and the metal electrode 11 formed on the layer containing organic compounds are stacked sequentially on the transparent substrate 15.

The organic electroluminescent device 1a shown in FIG. 2A exhibits a rectifying property. That is, when an electric field is applied with the metal electrode 11 being a cathode and the transparent electrode 14 being an anode, electrons from the metal electrode 11 and holes from the transparent electrode 14 are respectively injected toward the light-emitting layer 12. The injected holes and electrons reach the light-emitting layer 12, and are recombined in light-emitting molecules in the light-emitting layer 12. At this time, the light-emitting molecules generate excitons, and the excitons emit light when returning to a ground state. At this time, the hole-transporting layer 13 functions so as to block the electrons, so that the recombination efficiency at an interface between the light-emitting layer 12 and the hole-transporting layer 13 is increased. Therefore, compared with the organic electroluminescent device in which only the light-emitting layer is provided between electrodes, the emission efficiency is enhanced.

In an organic electroluminescent device 1b shown in FIG. 2B, an electron-transporting layer 16 is provided between the metal electrode 11 and the light-emitting layer 12 in the organic electroluminescent device 1a shown in FIG. 2A. The organic electroluminescent device 1b in FIG. 2B separates a layer having a light-emitting function from a layer having a function of either one of electron transportation and hole transportation. With this structure, carriers can be blocked more effectively, which can further enhance the emission efficiency.

In the organic electroluminescent device 1c shown in FIG. 2C, an exciton diffusion-prevention layer 17 is provided between the electron-transporting layer 16 and the light-emitting layer 12 in the organic electroluminescent device 1b shown in FIG. 2B. The organic electroluminescent device 1c shown in FIG. 2C can confine excitons in the light-emitting layer 12 efficiently by providing the exciton diffusion-prevention layer 17, so that the emission efficiency can be further enhanced.

The organic electroluminescent device of the present invention is not limited to the above embodiments. For example, an electron blocking layer and an acid diffusion-prevention layer may be provided between the hole-transporting layer and the light-emitting layer. These layers have functions of suppressing the leakage of electrons from the light-emitting layer, blocking ion components (acid components) from the hole-transporting layer side, thereby preventing them from reaching the light-emitting layer, and the like.

The organic electroluminescent device of the present invention contains a phosphorescent material of the present invention in a layer containing an organic compound, specifically, any one of the light-emitting layer 12, the hole-transporting layer 13, the electron-transporting layer 16, and the exciton diffusion-prevention layer 17 illustrated in FIGS. 2A to 2C. Preferably, the light-emitting layer 12 contains the phosphorescent material of the present invention. Further, the layer containing the phosphorescent material of the present invention may further contain other compounds, and the content thereof is not particularly limited.

Next, the materials constituting the respective layers of the organic electroluminescent device of the present invention will be described.

As the material for the transparent electrode 14, ITO or the like having a large work function is used. When the material having a large work function is used as a material for the transparent electrode 14, holes can be easily injected from the transparent electrode 14 to the hole-transporting layer 13.

As the material constituting the metal electrode 11, metal materials having a small work function, e.g., an elemental metal such as aluminum or magnesium, and an alloy thereof are used. When the material having a small work function is used as the material for the metal electrode 11, electrons can be easily injected from the metal electrode 11 to the organic layer, e.g., the electron-transporting layer 16.

Examples of the material constituting the light-emitting layer 12 include the phosphorescent material of the present invention, which may be mixed with other compounds.

Specifically, a known hole-transporting material, an electron-transporting material, or a light-emitting material may be used.

Specific examples of the hole-transporting material include triarylamine derivatives, phenylene diamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinylcarbazole), poly(silylene), and poly(thiophene).

Further, specific examples of the electron transporting material include organic compounds such as oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and an organic metal complex such as a quinolinol aluminum complex.

Further, examples of the light-emitting material include benzooxazole and its derivatives, benzoimidazole and its derivatives, benzothiazole and its derivatives, styrylbenzene and its derivatives, polyphenyl and its derivatives, diphenylbutadiene and its derivatives, tetraphenylbutadiene and its derivatives, naphthalimide and its derivatives, coumarin and its derivatives, a fused ring aromatic compound, perinone and its derivatives, oxadiazole and its derivatives, oxazine and its derivatives, aldazine and its derivatives, pyraridine and its derivatives, cyclopendadiene and its derivatives, bisstyryl anthracene and its derivatives, quinacridon and its derivatives, pyrrolopyridine and its derivatives, thiadiazolopyridine and its derivatives, styrylamine and its derivatives, diketopyrrolopyrrole and its derivatives, an aromatic dimethylidene compound, a metal complex that has 8-quinolinol and a derivative thereof as a ligand, a metal complex that has pyrromethene and a derivative thereof as a ligand, rare earth complexes, various kinds of metal complexes typified by transition metal complexes, polymer compounds such as polythiophene, polyphenylene, and polyphenylenevinylene, and an organic silane and its derivatives. Preferably, as a light-emitting material, a fused ring aromatic compound, a quinacridon derivative, a diketopyrrolopyrole derivative, a metal complex having a pyrromethene derivative as a ligand, a rare earth complex, and a transition metal complex are used, and more preferably, a fused ring aromatic compound and a transition metal complex are used.

Further, a phosphorescent material different from that of the present invention may also be used in combination. The phosphorescent material is preferably a transition metal complex. In the case of using a transition metal complex as a phosphorescent material, although the central metal of a complex is not particularly limited, iridium, platinum, rhenium, or ruthenium is preferably used. Specifically, an ortho-metallized complex disclosed by the following documents can be used.

1. Akio Yamamoto, "Organic metal, base and application" pp. 150 and 232, Shokabo Publishing Co., Ltd. (1982)
2. H. Yersin, "Photochemistry and Photophysics of Coordination Compound", pp. 71-77 and 135-146, Springer-Verlag (1987)
3. Japan Society for the Promotion of Science, "Organic Materials for Telecommunication Technology, 142$^{th}$ commission" C meeting (Organic electronics), 9$^{th}$ research meeting document, items 25 to 32 (2005)

In addition to the above, suitably usable phosphorescent materials are disclosed in patent documents such as U.S. Pat. Nos. 6,303,231 and 6,097,147, WO 00/57676A, WO 00/70655A, WO 01/08230A, WO 01/39234A, WO 01/41512A, WO 02/02714A, WO 02/15645A, Japanese Patent Application Laid-Open No. 2001-247859, Japanese Patent Application Nos. 2000-33561, 2001-189539, 2001-248165, 2001-33684, 2001-239281, and 2001-219909, European Patent No. 1211257, Japanese Patent Application Laid-Open Nos. 2002-226495, 2002-234894, 2001-247859, 2001-298470, 2002-173674, 2002-203678, and 2002-203679.

In addition, suitably usable phosphorescent materials are disclosed in non-patent documents such as Nature, Vol. 395, p. 151 (1998), Applied Physics Letters, Vol. 75, p. 4 (1999), Polymer Preprints, Vol. 41, p. 770 (2000), Journal of American Chemical Society, Vol. 123, p. 4304 (2001), and Applied Physics Letters, Vol. 79, p. 2082 (1999).

As the material constituting the hole-transporting layer 13, for example, polyethylenedioxythiophene/polystyrenesulphonate (PDOT/PSS) can be used.

As the material constituting the electron-transporting layer 16, for example, an oxadiazole derivative, a phenanthroline derivative, or an Al quinoinol complex can be used.

The method of producing the organic electroluminescent device of the present invention is not particularly limited. Specifically, the organic electroluminescent device can be produced by an evaporation method, a sputtering method, a CVD method, a thermal transfer method or a coating method (a spin coating method, an inkjet method, a printing method (offset printing, gravure printing, letterpress printing, intaglio printing, screen printing, etc.), a spraying method, a liquid development method having electrophotography applied thereto, etc.). In particular, it is preferred that a layer containing the phosphorescent material of the present invention is formed by a coating method.

The organic electroluminescent device of the present invention is applicable to a product which requires energy conservation and a high luminance. As application examples, an image display apparatus, a light source of a printer, an illumination apparatus, and a backlight of a liquid crystal display apparatus are conceivable.

An example of the image display apparatus includes an energy-saving, light-weight flat panel display with high visibility.

Further, as the light source of a printer, for example, a laser light source portion of a laser beam printer that has been currently used widely can be replaced by the organic electroluminescent device of the present invention. An example of a replacement method includes a method of placing an organic electroluminescent device that can be addressed independently on an array. Even if the laser light source portion is replaced by the organic electroluminescent device of the present invention, there is no particular difference in the formation of an image from a conventional example by conducting desired light exposure to a photosensitive drum. The volume of an apparatus can be reduced remarkably by using the organic electroluminescent device of the present invention.

Regarding the illumination apparatus and the backlight, the effect of energy conservation can be expected by using the organic electroluminescent device of the present invention.

Next, an image display apparatus of the present invention will be described. The image display apparatus of the present invention is obtained by combining the organic electroluminescent device of the present invention with thin film transistors. Further, the image display apparatus of the present invention is driven in accordance with a passive matrix system or an active matrix system.

Hereinafter, the image display apparatus of the present invention will be described in detail by exemplifying an active matrix system with reference to the drawings.

Figure 3:
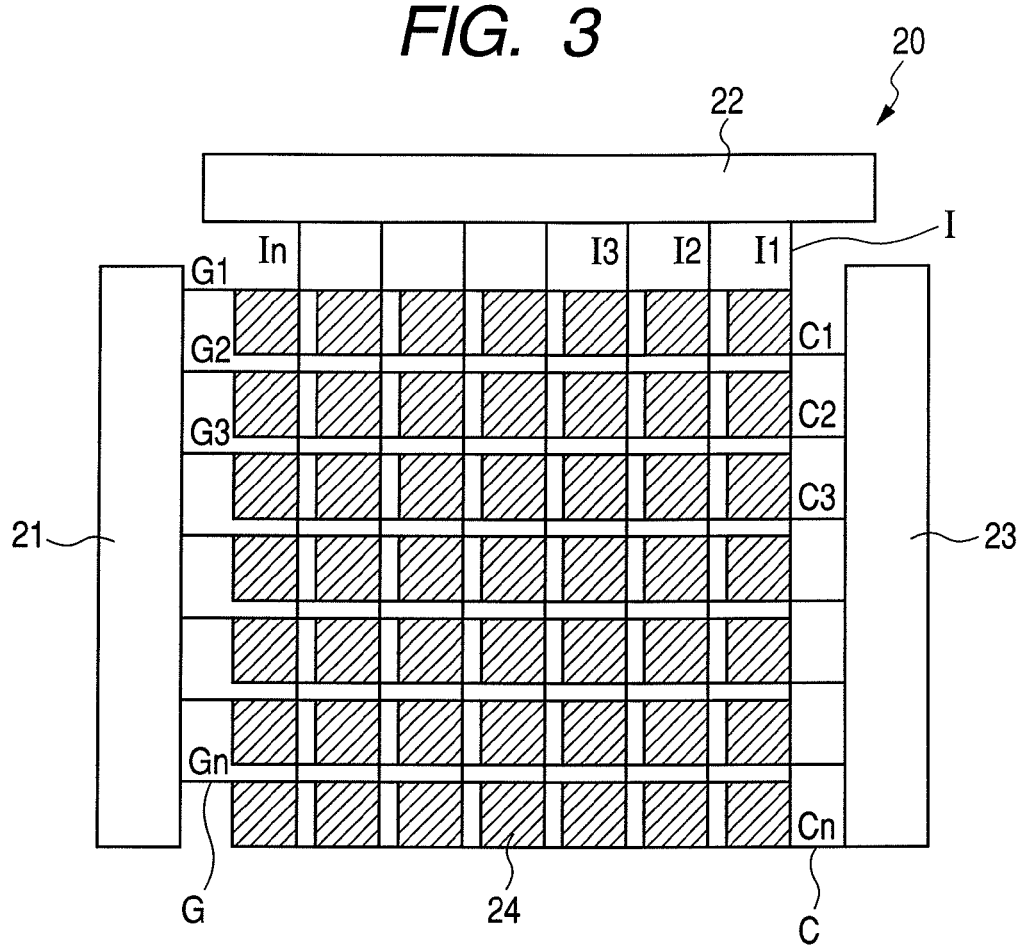
FIG. 3 is a view schematically illustrating one exemplary structure of an image display apparatus having the organic electroluminescent device and a driving unit of the present invention.

FIG. 3 is a view schematically illustrating an example of a configuration of an image display apparatus including the organic electroluminescent device of the present invention and a driving unit. In an image display apparatus 20 illustrated in FIG. 3, a scanning signal driver 21, an information signal driver 22, and a current supply source 23 are disposed, which are each connected to gate selection lines G, information signal lines I, and current supply lines C. A pixel circuit 24 is placed at a crossing point of the gate selection line G and the information signal line I. The scanning signal driver 21 successively selects gate selection lines G1, G2, G3, ... or Gn, and in synchronization therewith, an image signal is applied from the information signal driver 22 to the pixel circuit 24 through any of the information signal lines I1, I2, I3, ... or In.

Figure 4:
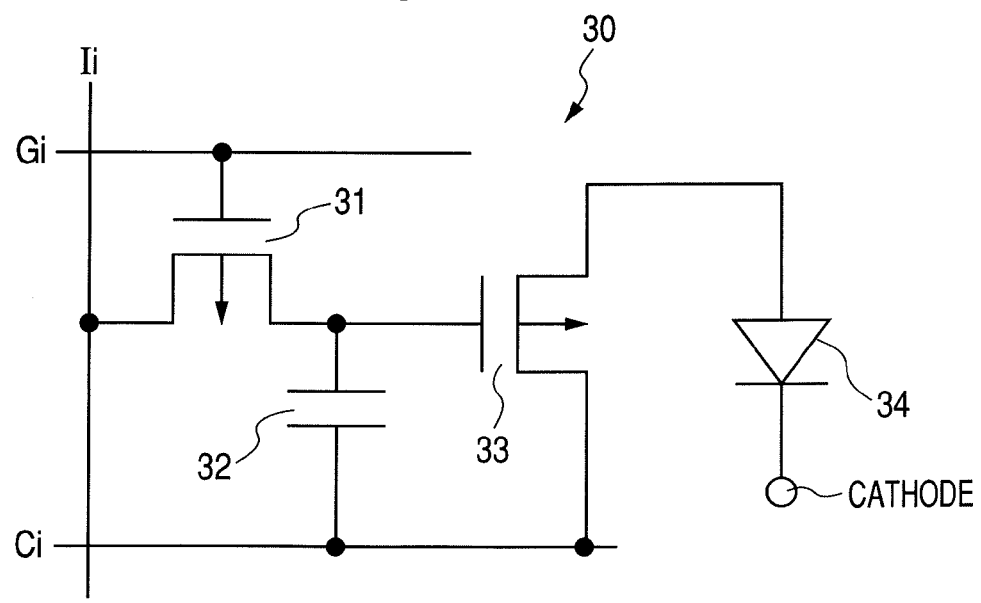
FIG. 4 is a circuit diagram illustrating a circuit constituting one of pixels disposed in the image display apparatus in FIG. 3.

Next, the operation of the pixels will be described. FIG. 4 is a circuit diagram illustrating a circuit constituting one of pixels disposed in the image display apparatus shown in FIG. 3. In a pixel circuit 30 shown in FIG. 4, when a selection signal is applied to the gate selection line G1, a first thin film transistor (TFT1) 31 is turned on, and an image signal Ii is supplied to a capacitor ($C_{add}$) 32, whereby a gate voltage of a second thin film transistor (TFT2) 33 is determined. A current is supplied to an organic electroluminescent device 34 from a current supply line Ci according to a gate voltage of the second thin film transistor (TFT2) 33. At this time, the gate potential of the second thin film transistor 33 is held at the capacitor ($C_{add}$) 32 until the first thin film transistor (TFT1) 31 is scanned and selected next. Therefore, a current continues to flow through the organic electroluminescent device 34 until the subsequent scanning is conducted. This enables the organic electroluminescent device 34 to emit light at all times during one frame.

Figure 5:
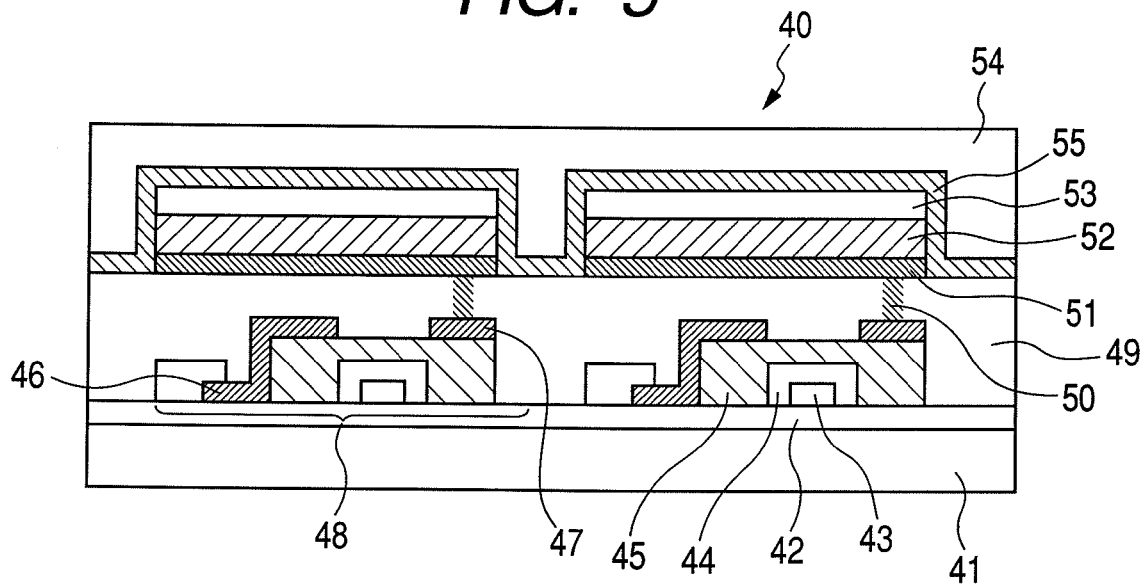
FIG. 5 is a schematic view illustrating an example of a cross-sectional structure of a TFT substrate used in the image display apparatus of the present invention.

FIG. 5 is a schematic view illustrating an example of a cross-sectional configuration of a TFT substrate used in the image display apparatus of the present invention. The detail of the configuration will be described by way of an example of the production process of a TFT substrate. When the image display apparatus 40 shown in FIG. 5 is produced, first, a substrate 41 formed of glass or the like is coated with a moisture-resistant film 42 for protecting a member (a TFT or an organic layer) formed in an upper portion. As a material constituting the moisture-resistant film 42, silicon oxide, a composite of silicon oxide and silicon nitride, or the like is used. Next, a metal such as Cr is formed into a film by sputtering and patterned to a predetermined circuit shape, whereby a gate electrode 43 is formed. Subsequently, silicon oxide or the like is formed into a film by a plasma CVD, a catalyst chemical vapor deposition (cat-CVD), or the like, and patterned to form a gate insulating film 44. Next, a silicon film is produced by Plasma CVD or the like (by annealing at a temperature of 290° C. or more in some cases), and patterned according to a circuit shape, whereby a semiconductor layer 45 is formed.

Further, a drain electrode 46 and a source electrode 47 are provided on the semiconductor film 45 to produce a TFT element 48, whereby a circuit as illustrated in FIG. 4 is formed. Next, an insulating film 49 is formed in an upper portion of the TFT element 48. Next, a contact hole (through-hole) 50 is formed so that an anode 51 for an organic electroluminescent device formed of a metal comes into contact with a source electrode 47.

A multi-layer or signal-layer organic layer 52 and a cathode 53 are sequentially stacked on the anode 51, whereby an image display apparatus 40 can be obtained. By driving the image display apparatus using the phosphorescent material of the present invention, a display of a satisfactory quality, which is stable during display for a long period of time, can be conducted.

Incidentally, in the image display apparatus of the present invention, there is no particular limit to a switching element, and a single-crystal silicon substrate, an MIM element, an a-Si type, or the like can be easily applied thereto.

EXAMPLES

Hereinafter, the present invention will be described specifically by way of examples. However, the present invention is not limited thereto. First, although the structures of phosphorescent materials used in the examples will be shown below, the present invention is not limited thereto.

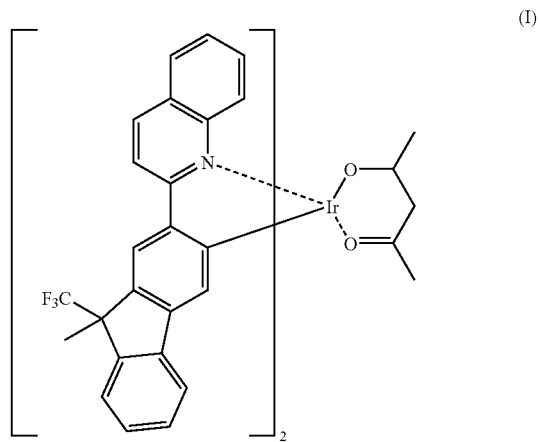

(I)

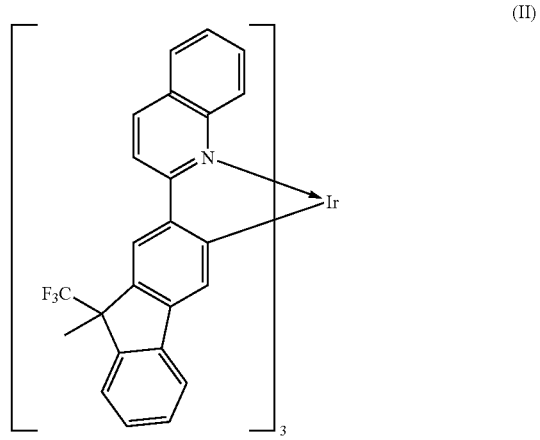

(II)

(III)
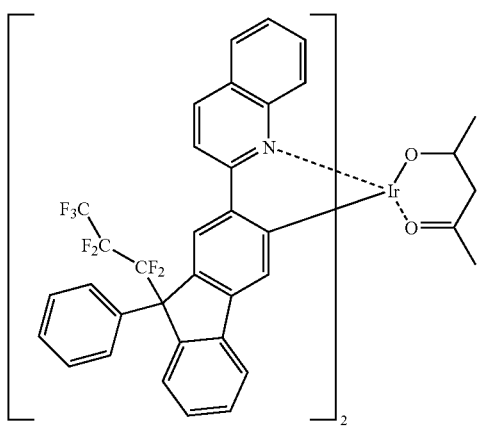
(IV)
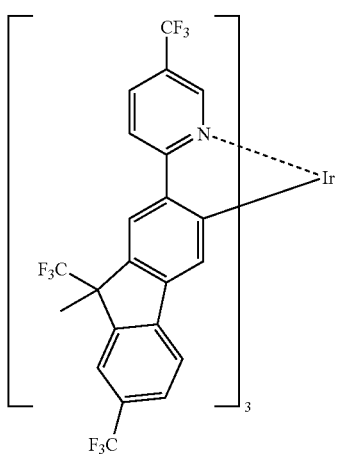
(V)
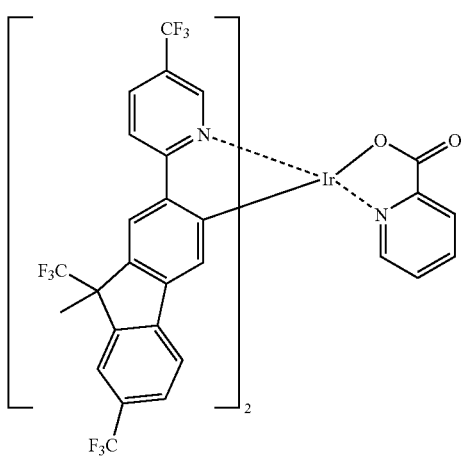
(VI)
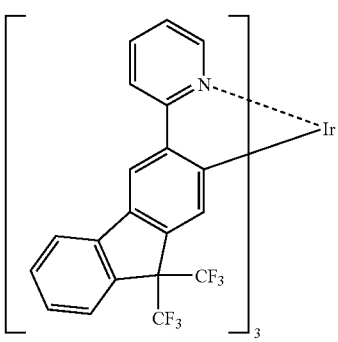
Next, the structural formulae of the compounds from (G1) to (G3) used in comparative example are shown below.
(G1)
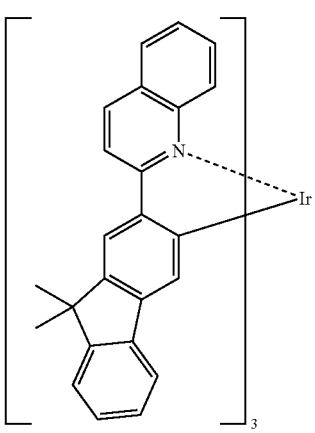
(G2)
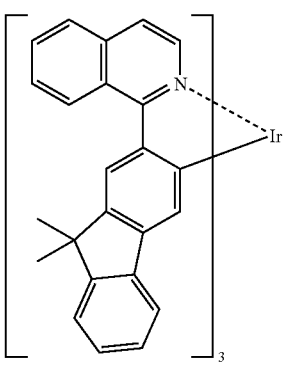
(G3)
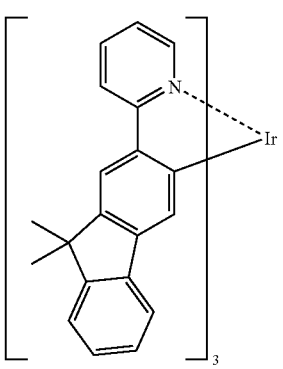

Herein, typical synthesis examples for synthesizing the compounds used in the examples will be shown below.

Example 1

Synthesis of Compound (I)

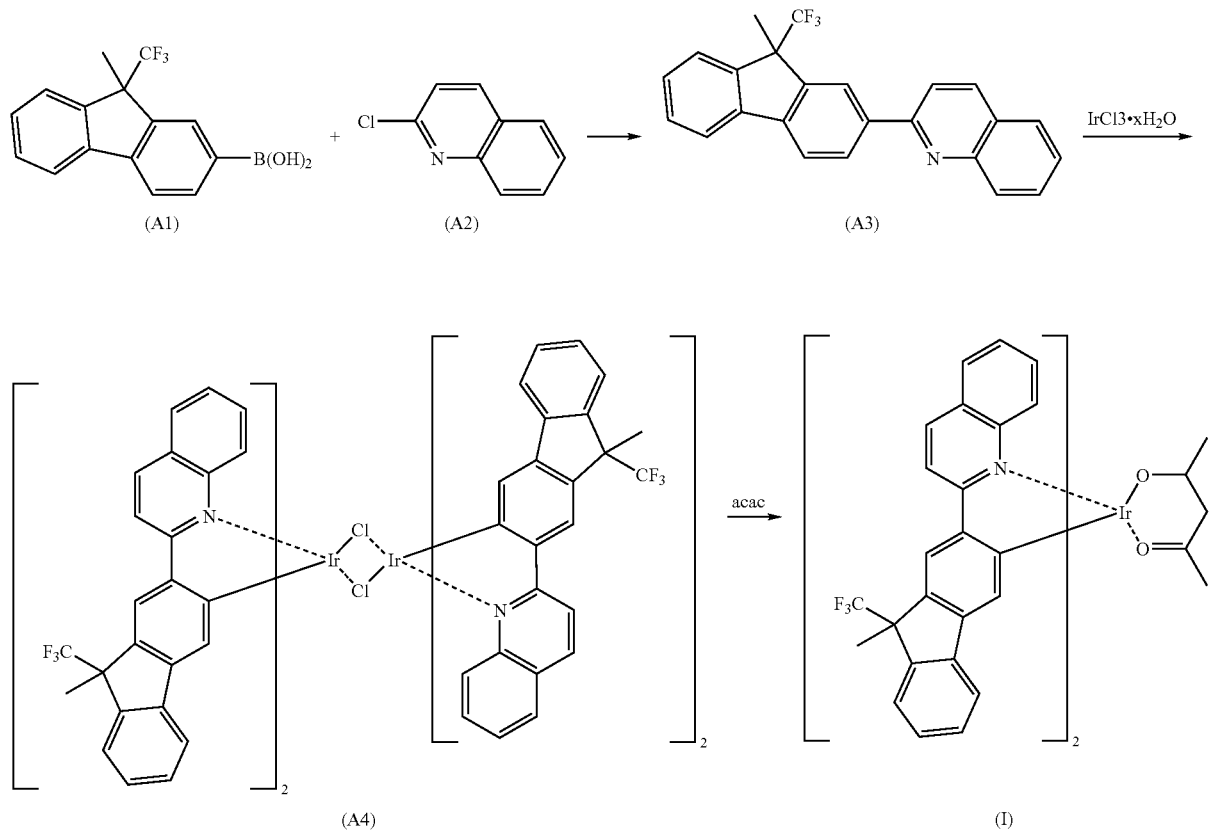

(1) The following reagents and solvents were placed in a 200 ml round bottom flask.

| | |
|---|---|
| Compound (A1): | 1.0 g (3.4 mmol) |
| Compound (A2): | 0.56 g (3.4 mmol) |
| Tetrakistriphenylphosphine palladium: | 0.1 g (0.08 mmol) |
| 2M-sodium carbonate aqueous solution: | 20 ml |
| Ethanol: | 20 ml |
| Toluene: | 80 ml |

Next, the reaction solution was stirred under nitrogen flow under heating and reflux for 6 hours. After the completion of the reaction, the reaction solution was poured into 100 ml of cold water, and then, 50 ml of toluene was added thereto to perform separation, whereby an organic layer was separated from a water layer. After that, the organic layer was concentrated under a reduced pressure. Next, the obtained solid substance was purified with silica gel column chromatography (developing solvent: toluene), and then recrystallized from hexane, whereby 1.1 g (yield 92%) of a white crystal of an intermediate compound (A3) was obtained.

(2) The following reagents and solvents were placed in a three-neck flask.

| | |
|---|---|
| Intermediate compound (A3): | 0.37 g (1.0 mmol) |
| Iridium (III) chloride hydrate: | 0.6 g |
| Ethoxyethanol: | 50 ml |
| Water: | 10 ml |

Next, the reaction solution was stirred under nitrogen flow at room temperature for 30 minutes, and thereafter, the reaction solution was stirred for 1 hour under reflux. After the completion of the reaction, the reaction solution was cooled to room temperature, and 50 ml of water was poured. The deposited precipitate was filtered off and washed with water and then washed with ethanol. Then, the precipitate was dried under a reduced pressure at room temperature, whereby 0.3 g (yield 61%) of a red powder of an intermediate compound (A4) was obtained.

(3) The following reagents and solvent were placed in a 200 ml three-neck flask.

| | |
|---|---|
| Ethoxyethanol: | 100 ml |
| Intermediate compound (A4): | 0.3 g (0.15 mmol) |
| Acetylacetone: | 0.04 g (0.38 mmol) |
| Sodium carbonate: | 0.08 g (0.8 mmol) |

Next, the reaction solution was stirred under nitrogen flow at room temperature for 1 hour, and thereafter, the reaction solution was stirred for 7 hours under reflux. After the completion of the reaction, the reaction solution was cooled with ice, and the deposited precipitate was filtered off and washed with water. The precipitate was washed with ethanol and dissolved in chloroform, and then an insoluble substance was filtered out. Then, the obtained filtrate was concentrated under a reduced pressure, and thereafter, recrystallized from chloroform-methanol, whereby 0.15 g (yield: 47%) of a red powder of compound (I) was obtained.

By MALDI-TOF MS, 1042 that was M+ of the compound was confirmed. The phosphorescent spectrum $\lambda_{max}$ in a toluene solution of the compound was 605 nm.

Further, assuming that the emission quantum efficiency of the following compound (G1)

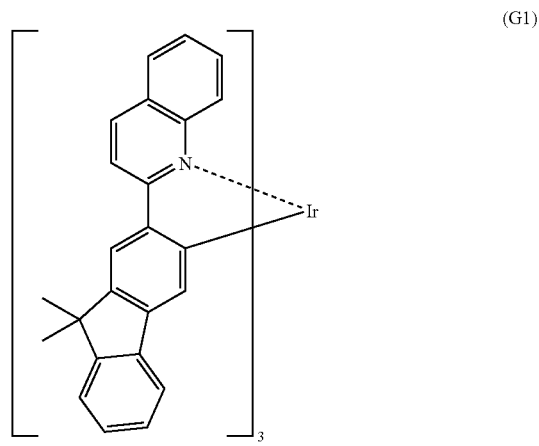

(G1)

is a reference ($\Phi$=1), the emission quantum efficiency of the compound (I) was $\Phi$=1.25. Incidentally, the emission quantum efficiency was measured with an external quantum efficiency measurement system utilizing an integrating sphere (C9920-12 (trade name): manufactured by Hamamatsu Photonics K.K.). Specifically, an emission quantum efficiency can be calculated from the ratio between the number of electrons (Ne) injected to the organic electroluminescent device per unit time and the number of photons (Np) per unit time released outside from the organic electroluminescent device (emission quantum efficiency=Np/Ne).

Example 2

Synthesis of Compound (II)

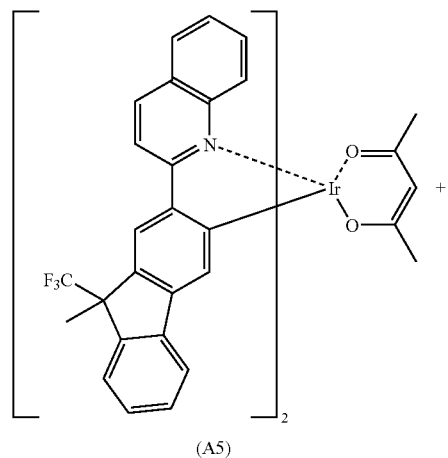

(A5)

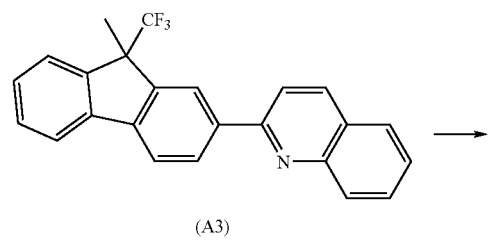

(A3)

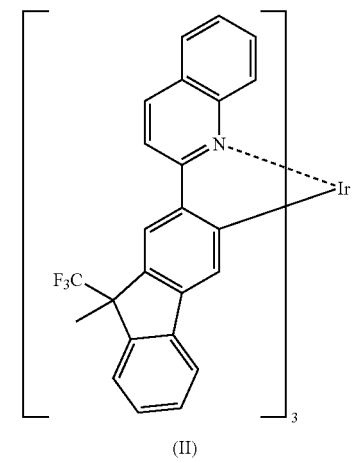

(II)

The following reagents and solvent were placed in a 100 ml three-neck flask.

| | |
|---|---|
| Compound (I): | 0.5 g (0.47 mmol) |
| Intermediate compound (A3): | 0.54 g (1.4 mmol) |
| Glycerol: | 20 ml |

Next, the reaction solution was stirred under nitrogen flow at a temperature at or near 180° C. for 8 hours. After the completion of the reaction, the reaction solution was cooled to room temperature, and thereafter, 100 ml of water was poured. Next, the deposited precipitate was filtered off and washed with water, and dried under a reduced pressure at 100° C. for 5 hours. The precipitate was purified with silica gel column chromatography using chloroform as a developing solvent, whereby 0.3 g (yield 48%) of a red powder of compound (II) was obtained.

By MALDI-TOF MS, 1042 that was M+ of the compound was confirmed. Further, the phosphorescent spectrum $\lambda_{max}$ in a toluene solution of the compound (II) was 607 nm.

Further, the quantum efficiency of the compound (II) was evaluated in the same way as in Example 1. The emission quantum efficiency of the compound (II) was $\Phi$=1.23 assuming that the emission quantum efficiency of the above compound (G1) is a reference ($\Phi$=1).

Example 3

Synthesis of Compound (III)

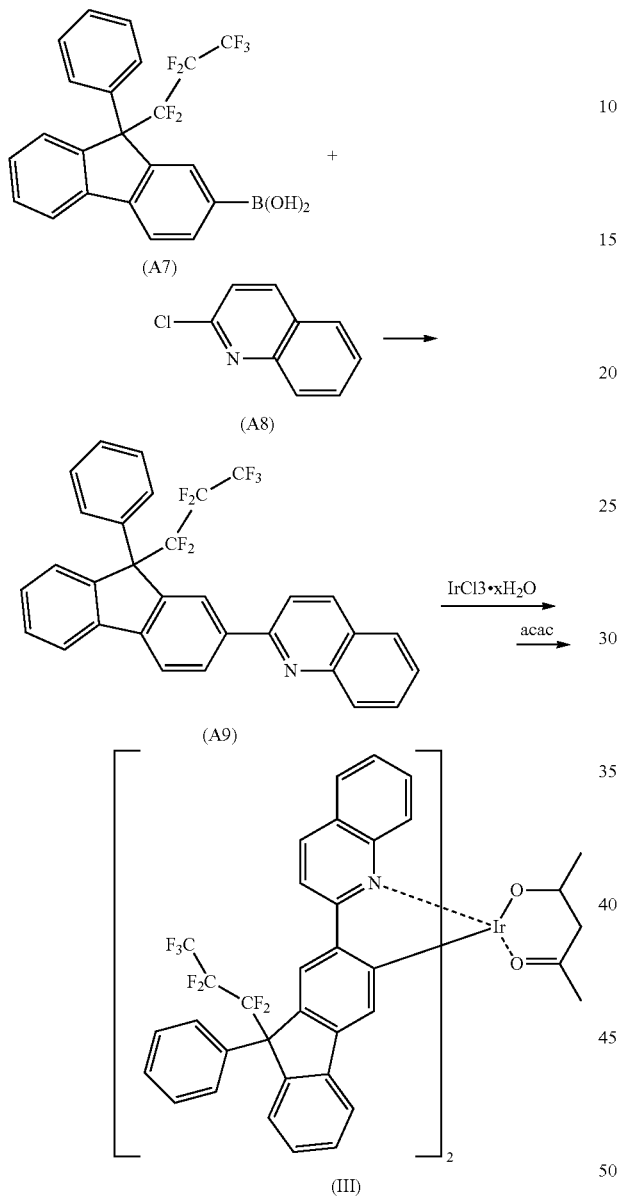

(1) The following reagents and solvent were placed in a 200 ml round bottom flask. Incidentally, a compound (A7) was synthesized by the synthesis method described in Journal of Organic Chemistry, 65(22), 7703-7706 (2000).

| | |
|---|---|
| Compound (A7): | 1.0 g (2.2 mmol) |
| Compound (A8): | 0.36 g (2.2 mmol) |
| Tetrakistriphenylphosphine palladium: | 0.1 g (0.08 mmol) |
| 2M-sodium carbonate aqueous solution: | 20 ml |
| Ethanol: | 20 ml |
| Toluene: | 80 ml |

Next, the reaction solution was stirred under nitrogen flow under heating and reflux for 6 hours. After the completion of the reaction, the reaction solution was poured into 100 ml of cold water, and then, 50 ml of toluene was added thereto to perform separation, whereby an organic layer was separated from a water layer. After that, the organic layer was concentrated under a reduced pressure. Next, the obtained solid substance was purified with silica gel column chromatography (developing solvent: toluene), and then recrystallized from hexane, whereby 0.93 g (yield 79%) of a white crystal of an intermediate compound (A9) was obtained.

(2) 0.08 g (yield 6.8%) of a red powder of compound (III) was obtained by following the same synthesis procedure as in Example 1 with the exception that 0.93 g of an intermediate compound (A9) was used in place of the intermediate compound (A3) in Example 1(3).

By MALDI-TOF MS, 1366 that was M+ of the compound was confirmed. Further, the phosphorescent spectrum $\lambda_{max}$ in a toluene solution of the compound (III) was 605 nm.

Further, the quantum efficiency was evaluated in the same way as in Example 1. The emission quantum efficiency of the compound (III) was $\Phi=1.24$ assuming that the emission quantum efficiency of the compound (G1) is a reference ($\Phi=1$).

Example 4

Synthesis of Compound (IV)

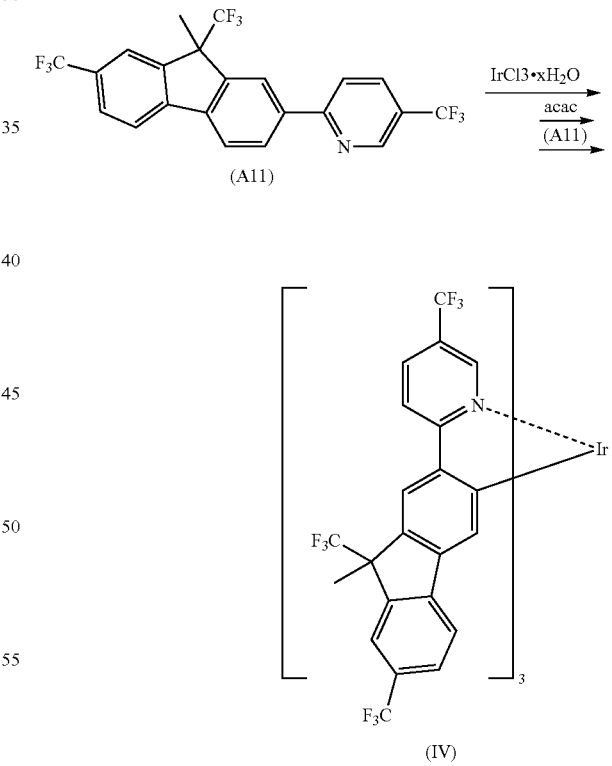

An organic metal complex containing a compound (A11) and acetylacetone (acac) in a ratio of 2:1 was obtained by following the same synthesis procedure as in Example 1 with the exception that 1.0 g of the compound (A11) was used in place of the intermediate compound (A3) in Example 1(2). Then, 0.58 g of the compound (II) was allowed to react with respect to the organic metal complex by the same synthesis method as that in Example 2, whereby 0.22 g (yield 13%) of the yellow powder of compound (IV) was obtained.

By MALDI-TOF MS, 1369 that was M+ of the compound was confirmed. Further, the phosphorescent spectrum $\lambda_{max}$ in a toluene solution of the compound (IV) was 525 nm.

Further, the quantum efficiency was evaluated in the same way as in Example 1. The emission quantum efficiency of the compound (IV) was $\Phi=1.26$ assuming that the emission quantum efficiency of the compound (G3) is a reference ($\Phi=1$).

Example 5

Synthesis of Compound (V)

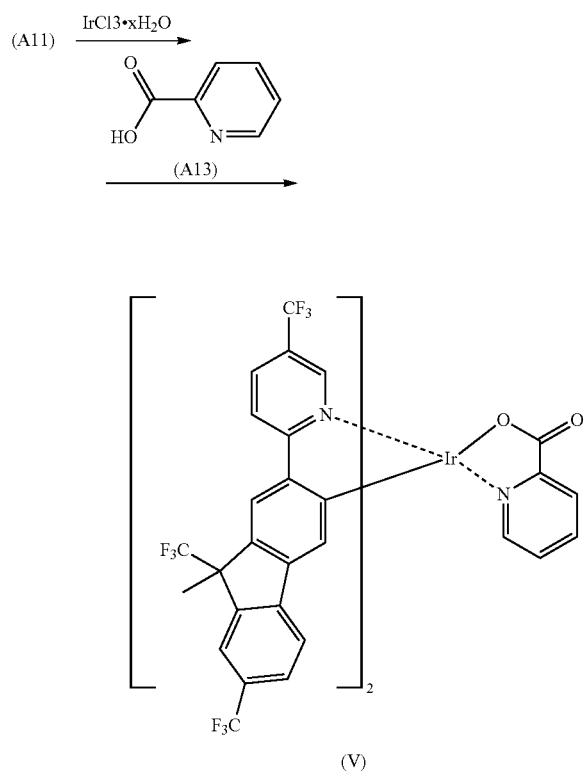

(V)

A complex synthesis reaction in a first stage was performed by following the same synthesis procedure as in Example 1 with the exception that 1.0 g of the compound (A11) was used in place of the intermediate compound (A3) in Example 1(2). Then, 0.25 g (yield 14%) of a yellow powder of compound (V) was obtained by following the same synthesis procedure as in Example 1 with the exception that a compound (A13) was used in place of the acac.

By MALDI-TOF MS, 1369 that was M+ of the compound was confirmed. Further, the phosphorescent spectrum $\lambda_{max}$ in a toluene solution of the compound (V) was 515 nm.

Further, the quantum efficiency was evaluated in the same way as in Example 1. The emission quantum efficiency of the compound (V) was $\Phi=1.18$ assuming that the emission quantum efficiency of the compound (G3) is a reference ($\Phi=1$).

Example 6

Synthesis of Compound (VI)

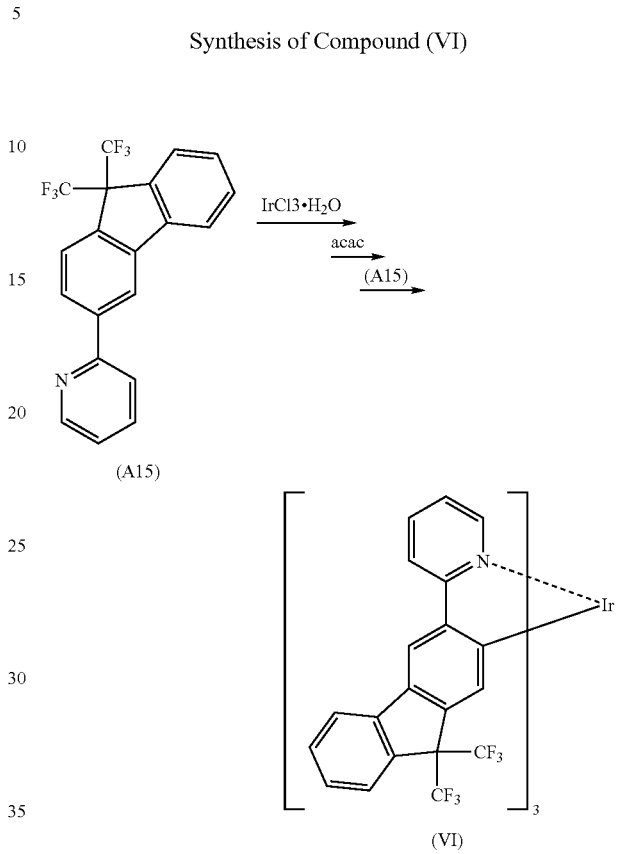

An organic metal complex containing a compound (A15) and the acac in a ratio of 2:1 was obtained by following the same synthesis procedure as in Example 1 with the exception that 3.0 g of the compound (A15) was used in place of the intermediate compound (A3) in Example 1(2). Then, 0.60 g of the compound (A15) was allowed to react with the organic metal complex by following the same synthesis procedure as in Example 2, whereby 0.35 g (yield 10%) of a yellow powder of compound (VI) was obtained.

By MALDI-TOF MS, 1380 that was M+ of the compound was confirmed. Further, the phosphorescent spectrum $\lambda_{max}$ in a toluene solution of the compound (VI) was 521 nm.

Further, the quantum efficiency was evaluated in the same way as in Example 1. The emission quantum efficiency of the compound (VI) was $\Phi=1.32$ assuming that the emission quantum efficiency of the compound (G3) is a reference ($\Phi=1$).

Example 7

Production of an Organic Electroluminescent Device

An organic electroluminescent device having 3 organic layers shown in FIG. 2B was produced as follows. First, ITO was patterned as the transparent electrode 14 so as to have a thickness of 100 nm and an electrode area of 3.14 mm$^2$ on a glass substrate (transparent substrate 15). On the substrate having the ITO patterned thereon, organic layers and a metal electrode layer were stacked by spin coating or vacuum deposition under a reduced pressure of $10^{-4}$ Pa according to the procedure described below to produce the device.

Specifically, PEDOT/PSS Al 4083 (trade name; manufactured by Baytron Ltd.) was formed to a film on the ITO substrate as the hole-transporting layer 13 by spin coating. When the film was formed by spin coating, the ITO substrate was rotated at a rotation speed of 2000 rpm for 2 minutes under a nitrogen atmosphere. After the film was formed, it was dried at 200° C. The thickness of the hole-transporting layer 13 after being dried was 400 Å.

Next, a layer containing the compound (I) was formed as the light-emitting layer 12. Specifically, the compound (I) was weighed so as to be 4% by weight with respect to poly (9,9-di-n-hexylfluorenyl-2,7'-diyl)(PFL)(57104-0 (trade name); manufactured by Sigma-Aldrich Co.), whereby 0.2% by weight of a toluene solution of the mixture was prepared. Next, the thus prepared solution was formed into a film by spin coating. The solution was formed into a film in a nitrogen atmosphere while being rotated at a rotation speed of 1000 rpm for one minute, followed by drying at 80° C. The thickness of the light-emitting layer 12 after being dried was 400 Å.

Next, as the electron-transporting layer 16, Bphen (manufactured by Sigma-Aldrich Co.) was formed into a film. At this time, the thickness of the electron-transporting layer 16 was set to be 200 Å.

Next, as the metal electrode 11, LiF was formed into a film having a thickness of 10 Å by vapor deposition. Al was formed to a film having a thickness of 1200 Å on the metal electrode 11 by vapor deposition. Thus, an organic electroluminescent device was obtained.

The thus obtained device was evaluated for its performance by the following method.

(i) Emission Wavelength

The emission wavelength was measured by a spectrophotometer (F-4500 (trade name); manufactured by Hitachi High-Technologies Corporation) with respect to the phosphorescent material compound of the present invention dissolved in toluene to a predetermined concentration ($10^{-5}$ to $10^{-4}$ mol/l)

(ii) Current Efficiency

The current efficiency was measured by an organic EL emission characteristics evaluation apparatus (Cradle Corp.) with respect to the organic electroluminescent device of the present invention. This apparatus is composed of a camera obscure, a luminance meter, a multichannel spectroscope, a device driving power source, and an analyzer. Data regarding the luminance, current-luminance characteristics, voltage-luminance characteristics, and voltage-current characteristics of the device is obtained by controlling a driving current and a driving voltage to the device with a program. The apparatus can measure the current efficiency.

(iii) Luminance Half-Life Period

The luminance half-life period was measured using the same apparatus as with the case of the above current efficiency measurement. That is, the initial luminance of the device of the present invention was set to be 1000 cd/A, and the time during which the luminance was attenuated to 50% was defined to be a luminance half-life period.

(iv) Emission Unevenness

The emission unevenness was obtained by visually observing a light-emitting plane when 1 mA of a current was flowed in the device of the present invention to allow the device to emit light and checking the presence/absence of dark spots.

In the organic electroluminescent device of the present example, the current efficiency and the power efficiency at a luminance of 1000 cd/m$^2$ were 14 cd/A and 131 m/W, respectively. The peak of an emission spectrum of light emitted from the device was 605 nm.

Examples 8 to 12

Devices were produced by following the same procedure as in Example 7 with the exception that the compounds (II) to (VI) were, respectively, used in place of the compound (I) as a phosphorescent material to be contained in the light-emitting layer 12 in Example 7. The thus obtained devices were each evaluated in the same way as in Example 7. Table 1 shows the evaluation results.

Comparative Examples 1 to 3

Devices were produced by following the same procedure as in Example 10 with the exception that the compounds (G1) to (G3) were, respectively, used in place of the compound (I) as a phosphorescent material to be contained in the light-emitting layer 12 in Example 7. The thus obtained devices were evaluated in the same way as in Example 7. Table 1 shows the evaluation results.

TABLE 1

| | | Device Evaluation | | | |
|---|---|---|---|---|---|
| | Light-emitting layer | Emission wavelength (nm) | Current efficiency (cd/A) during driving at 1000 cd/m$^2$ | Luminance half-life period (hr) at start of 1000 cd/m$^2$ | Emission unevenness (presence/absence of darksports) |
| Ex. 7 | Compd. I + PFL | 610 | 17 | 220 | Absence |
| Ex. 8 | Compd. II + PFL | 612 | 15 | 210 | Absence |
| Ex. 9 | Compd. III + PFL | 610 | 16 | 215 | Absence |
| Ex. 10 | Compd. IV + PFL | 523 | 21 | 167 | Absence |
| Ex. 11 | Compd. V + PFL | 515 | 13 | 155 | Absence |
| Ex. 12 | Compd. VI + PFL | 524 | 16 | 182 | Absence |
| Comp. Ex. 1 | Compd. G1 + PFL | 623 | 10 | 98 | Presence(*Note 1) |
| Comp. Ex. 2 | Compd. G2 + PFL | 652 | 3 | 18 | Presence(*Note 1) |

TABLE 1-continued

| | Light-emitting layer | Emission wavelength (nm) | Current efficiency (cd/A) during driving at 1000 cd/m² | Luminance half-life period (hr) at start of 1000 cd/m² | Emission unevenness (presence/absence of darksports) |
|---|---|---|---|---|---|
| Comp. Ex. 3 | Compd. G3 + PFL | 545 | 11 | 75 | Presence(*Note 1) |

*(Note 1) Ir complex crystallized

It can be seen from the above table that emission unevenness and dark spots (non-lighting portions) were observed in the devices using the phosphorescent materials having no fluorine-containing alkyl group in a fluorene moiety that is a partial structure of a ligand, i.e., the compounds (G1) to (G3). Further, the compounds (G1) to (G3) were observed to be aggregated (crystallized) in poly(9,9-di-n-hexylfluorenyl-2,7'-diyl).

Further, the device using the compound (G2) emitted light having an emission peak of 660 nm and exhibiting a dark red color containing a purple color, and the efficiency of the device was low. Meanwhile, the device using the compound (G3) emitted light having an emission peak of 560 nm and exhibiting a yellow green color. Thus, in any case, red light or green light of a high purity was not exhibited.

As described above, an Ir complex or a Pt complex (phosphorescent material of the present invention) containing as a ligand a compound obtained by combining a fluorene skeleton, a fluorenylpyridine skeleton, a fluorenylquinoline skeleton, or a fluorenylisoquinoline skeleton having a fluorine-containing substituent is excellent in solubility. Therefore, a film can be formed easily by a known coating method. Further, the organic electroluminescent device of the present invention using the phosphorescent material of the present invention is an excellent device having a high efficiency and high durability. Further, the organic electroluminescent device of the present invention is also excellent as a display device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-142915, filed May 30, 2007, which is hereby incorporated by reference herein in its entirety.

What is claimed is:

1. A phosphorescent material comprising an Ir complex having at least one ligand represented by general formula (1):

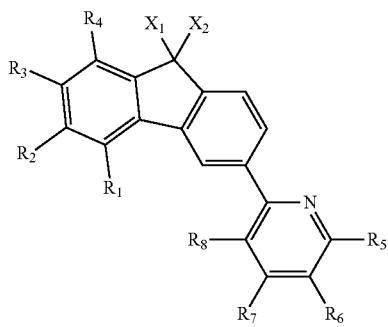

(1)

where $X_1$ and $X_2$ are $CF_3$; and $R_1$, $R_2$, $R_3$, $R_4$, $R_5$, $R_6$, $R_7$, and $R_8$ each represent, independently of one another, a hydrogen atom, a halogen atom, or an alkyl group having 1 to 20 carbon atoms.

2. An organic electroluminescent device comprising:

an anode and a cathode; and a layer comprising an organic compound interposed between the anode and the cathode, wherein the layer comprises the phosphorescent material set forth in claim 1.

3. The organic electroluminescent device according to claim 2, wherein the layer containing the phosphorescent material is formed by a coating method.

4. The organic electroluminescent device according to claim 2, wherein the phosphorescent material is contained in a light-emitting layer.

5. An image display apparatus which comprises the organic electroluminescent device set forth in claim 2 and a thin film transistor and which is driven in accordance with a passive matrix system or an active matrix system.

6. A compound represented by the following structure:

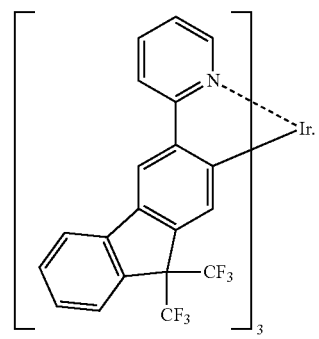

7. An organic electroluminescent device comprising:

an anode and a cathode; and a layer comprising an organic compound interposed between the anode and the cathode, wherein the layer comprises the phosphorescent material set forth in claim 6.

* * * * *